United States Patent [19]

Chiles, III

[11] 4,244,021
[45] Jan. 6, 1981

[54] ERGOMETRIC EXERCISER

[75] Inventor: Robert E. Chiles, III, Sterling, Va.

[73] Assignee: AMF Incorporated, White Plains, N.Y.

[21] Appl. No.: 16,734

[22] Filed: Mar. 2, 1979

[51] Int. Cl.³ .......................... G01L 5/02; G06F 15/42
[52] U.S. Cl. ...................................... 364/413; 73/379; 272/73; 272/DIG. 6; 340/384 E
[58] Field of Search ................. 364/413, 415; 73/379; 272/73, DIG. 6; 235/92 MT; 340/384 R, 384 E, 328, 309.1, 309.4

[56] References Cited

U.S. PATENT DOCUMENTS

| 3,511,097 | 5/1970 | Corwin | 73/379 |
| 3,767,195 | 10/1973 | Dimick | 272/DIG. 6 |
| 3,802,698 | 4/1974 | Burian et al. | 272/73 |
| 3,848,467 | 11/1974 | Flavell | 73/379 |
| 3,859,840 | 1/1975 | Gause | 73/379 |
| 3,973,251 | 8/1976 | Stephas | 272/73 |
| 4,141,248 | 2/1979 | Bargenda | 73/379 |
| 4,149,526 | 4/1979 | Bargenda et al. | 128/706 |

OTHER PUBLICATIONS

Jacobsen et al., "An Ergometer Bicycle Controlled by Heart Rate", Medical and Biological Engineering, Sep. 1974, pp. 675–680.

Primary Examiner—Errol A. Krass
Attorney, Agent, or Firm—George W. Price; Lawrence Hager

[57] ABSTRACT

An ergometric exerciser of the constant work type using a mechanical to electrical transducer as its basis is described. The exerciser is controlled by a single chip microcomputer and associated electronic interfacing means to perform a multiplicity of selected functions. For example, the ergometric exerciser provides; adjustable work loading from 300 to 2100 kpm per minute; a flashing indicator light to warn of a low pedal speed; a pulse rate measurement from 40 to 200 beats per minute; a sonic pulse alert system adjustable from 60 to 200 beats per minute; an accurate electronic start/stop timer adjustable from 1:00 to 60:00 minutes; and a microcomputer controlled work computer which accurately calculates work done to a maximum of 99,990 kpm. All of the above functions can be conveniently performed by virtue of a control panel and visual display which is very easy to use to accurately and efficiently perform the above functions.

25 Claims, 32 Drawing Figures

TO U4, PIN 10
(FIG. 12B)

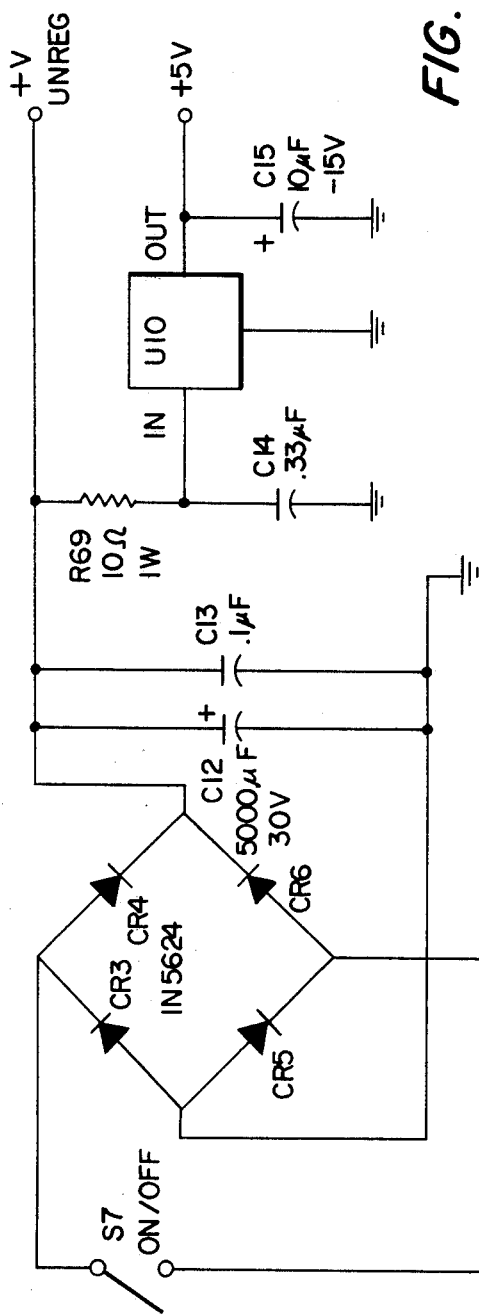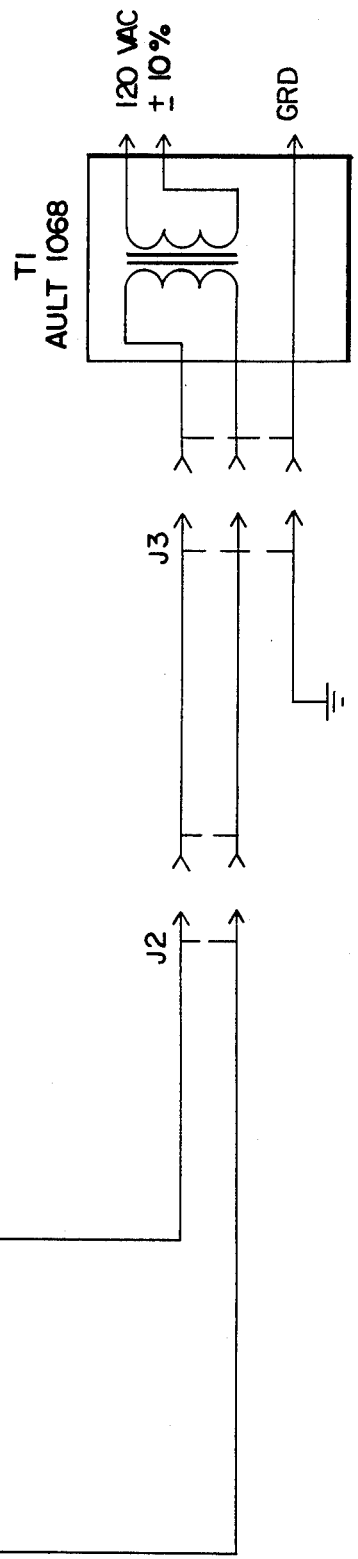
FIG. 12F

ERGOMETRIC EXERCISER

BACKGROUND OF THE INVENTION

The present invention relates to a bicycle-type exerciser device hereinafter referred to as an ergometric exerciser.

An ergometric exerciser is a device which controls and measures work. The word "ergometric" derives from the Greek words "ergon" meaning "work" and "metric" relating to measurement. The majority of exercisers available today can not be classed as ergometric, since they are not designed to maintain a constant work loading. Many use a simple spring loaded wheel or belt arrangement to provide friction loading for a bicycle-type wheel which is mechanically driven by the user. True ergometric exercisers have been designed using purely mechanical techniques to accomplish and measure the work loading. A practical type measures torque using a mechanical arrangement called a sinus balance. This ergometer is designated as a constant torque type and requires that the user pedal at a constant rate in order to maintain a constant work load.

Another type of ergometer operates on the principle of energy transformation and converts mechanical work into electrical work using a suitable transducer. While additional sources of errors may be introduced with this method, there are many advantages to it. The primary advantage involves the relative ease of controlling and measuring the work done. In addition, an ergometer of this type can be designed to avoid the requirement for the operator to pedal at a constant rate. This type of ergometer is then known as a constant work type.

All of the ergometric exercisers known heretofore either are limited in the number of functions which can be performed during an exercise routine, or if a multiplicity of functions are available, the device is extremely complicated to operate. Thus, the use of all of the device functions is discouraged by the complexity of the operating controls.

SUMMARY OF THE INVENTION

Accordingly, it is a primary object of the present invention to provide an ergometric exerciser which is computer controlled to provide a large selection of functions for an exercise routine.

It is a further object of the present invention to provide a simplistic and well organized control panel and display format for the various control functions which encourages a user to utilize all available functions.

It is still a further object of the present invention to provide novel input and output means on the control panel which interface with the computer controller to make the exerciser extremely convenient and easy to operate.

It is another object of the present invention to provide an ergometric exerciser which automatically tests the functional components of the control panel and display elements thereon when power is first applied to the exerciser.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

The ergometric exerciser of the present invention is a stationary bicycle ergometer of the constant work type which uses a mechanical to electrical transducer as its basis. In addition, it is totally controlled by an electronic system using a single chip microcomputer. Work performed is regulated to be essentially a constant value as selected by the user for pedal speeds above certain minimums. A control panel light flashes an indication to the user if his pedal speed falls below the minimums.

The work loading range of the exerciser of the present invention is from 300 to 2100 kilopond meters/minute and the actual work done against time then has units of kilopond meters. The kilopond meter is a metric unit commonly used in the medical field. It is derived as follows. The kilopond is a unit of force; one kilopond is the force acting on a mass of one kilogram at normal acceleration of gravity. The corresponding unit of work is the kilopond meter (kpm). The kilopond meter per minute is then the unit of power. Thus a kilopond meter is the work done in lifting one kilogram (2.2 pounds) one meter (39.4 inches) at normal gravity. In more familiar units, 300 kpm per minute equals about 49 watts or 0.066 horsepower. The exerciser of the present invention provides 10 work loads over a 300 to 2100 kmp per minute range. These work loads are constant and independent of the user influence above the minimum pedal speeds.

The exerciser of the present invention is designed to be a total exercise machine by allowing the user to conveniently and accurately control and measure his responses to the exercise process. To do this the exerciser provides at least the following capabilities:

Adjustable work loading from 300 to 2100 kpm per minute;

Flashing indicator light to warn of low pedal speed;

Pulse rate measurement from 40 to 200 beats per minute;

A sonic pulse alert system adjustable from 60 to 200 beats per minute;

An accurate electronic start/stop timer adjustable from 1:00 to 60:00 minutes; and A microprocessor controlled work computer which accurately calculates work done to a maximum of 99,990 kpm.

The user may conveniently cause the exerciser of the present invention to perform the above functions by virtue of the unique control panel and display format of the present invention. One digital display unit is provided which is time-share multiplexed by the various data functions or modes. That is, the digital display will display different units depending on the data mode selected. A plurality of LED indicator lamps, one for each data mode, in conjunction with the digital display inform the user of the units and magnitude, respectively, of the data displayed. For example, if the LED associated with the data mode which programs or computes work is illuminated, the digital data displayed is in units of kilopond meters.

The various data modes may be selected in sequence in accordance with the positional arrangement of the associated LED indicator lamps by each actuation of a single display select button. That is, each actuation of a display select button steps the indicator lamps one step for each actuation to put the exerciser in a different selected date mode.

The control panel of the present invention also provides a convenient set of programming switches used in conjunction with the visual display. The programming switches include a slow set, fast set, and reverse set pushbutton to increment or decrement the digital display as desired.

BRIEF DESCRIPTION OF THE DRAWINGS

The present invention will become more fully understood from the detailed description given hereinbelow and the accompanying drawings which are given by way of illustration only, and thus are not limitative of the present invention and wherein:

FIG. 10 is a diagrammatic view illustrating the microcomputer input-output port assignments of the microcomputer of FIG. 9;

FIGS. 12A to 12F are a detailed schematic drawing of all of the electronic circuitry contained with the ergometric exerciser of the present invention illustrating the interfacing of that circuitry with the microcomputer of FIG. 9.

DETAILED DESCRIPTION OF THE DRAWINGS

Figure 1:
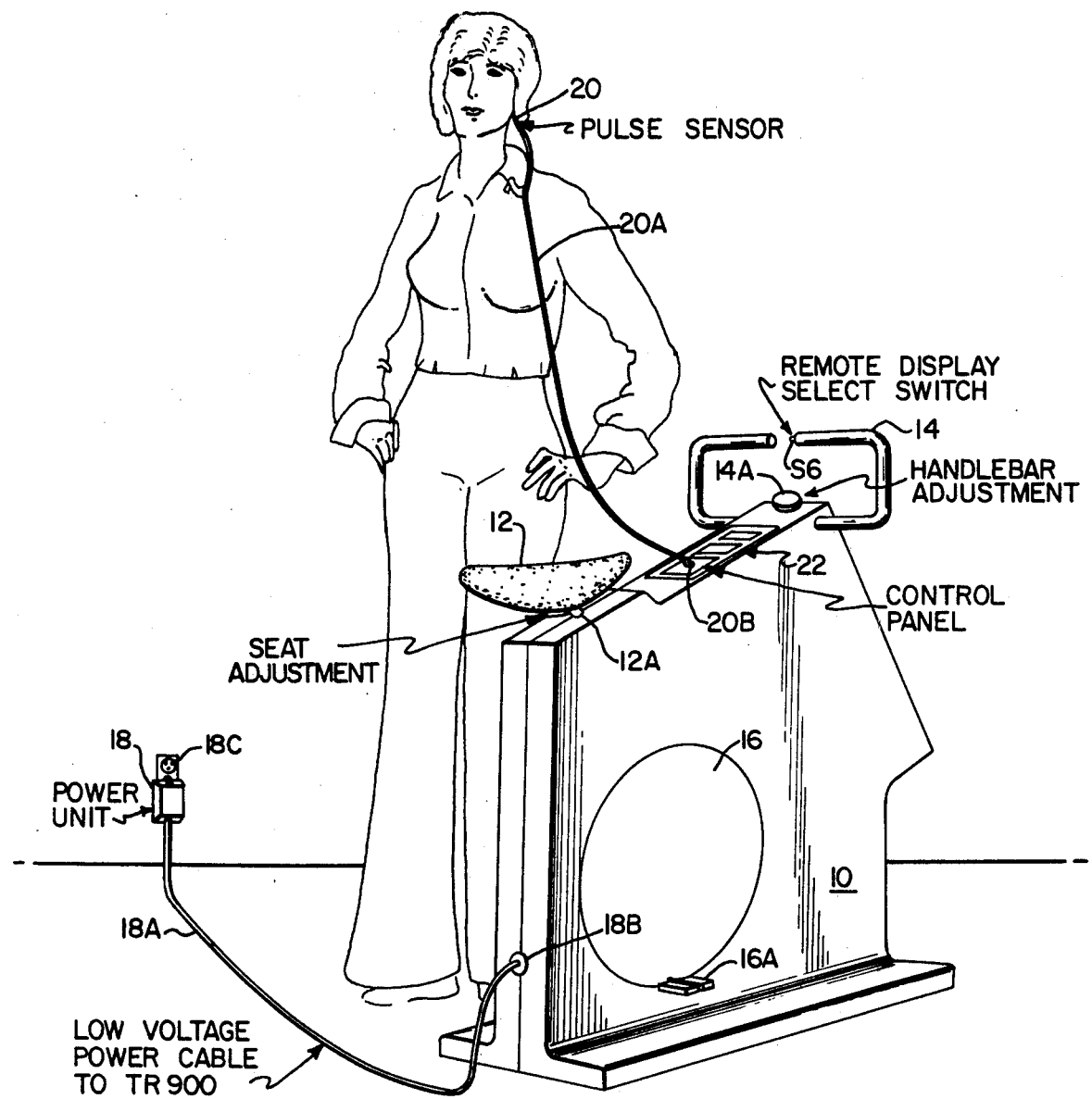
FIG. 1 is a perspective view of the mechanical features of the ergometric exerciser of the present invention.

Referring in detail to the drawings and with particular reference to FIG. 1, there is depicted an ergometric exerciser unit 10 having a seat 12, handlebars 14, both of these being adjustable by respective conventional adjustment means 12A and 14A, respectively, to allow the user to obtain a comfortable operating position on the exerciser. A pedal assembly 16 having pedals 16A is provided to drive the exerciser unit 10. Preferably, the knee joint of a user should be slightly bent at the bottom of travel of the pedals 16A with the body leaning forward slightly in a relaxed position on the seat 12. A power cord 18A from a power unit 18 leads into a socket 18B on the back of the exerciser 10 and the power unit 18 is plugged into a wall socket 18C furnishing standard 120 V, 60 Hz power. Note that only low 12 VAC power connects to the exerciser through the power unit 18 which is a step down device. A pulse sensor 20 has a cable 20A extending from a socket 20B on the control panel 22 of the exerciser 10 and the sensor clips over either ear lobe of a user by a suitable clamping means.

Figure 2:
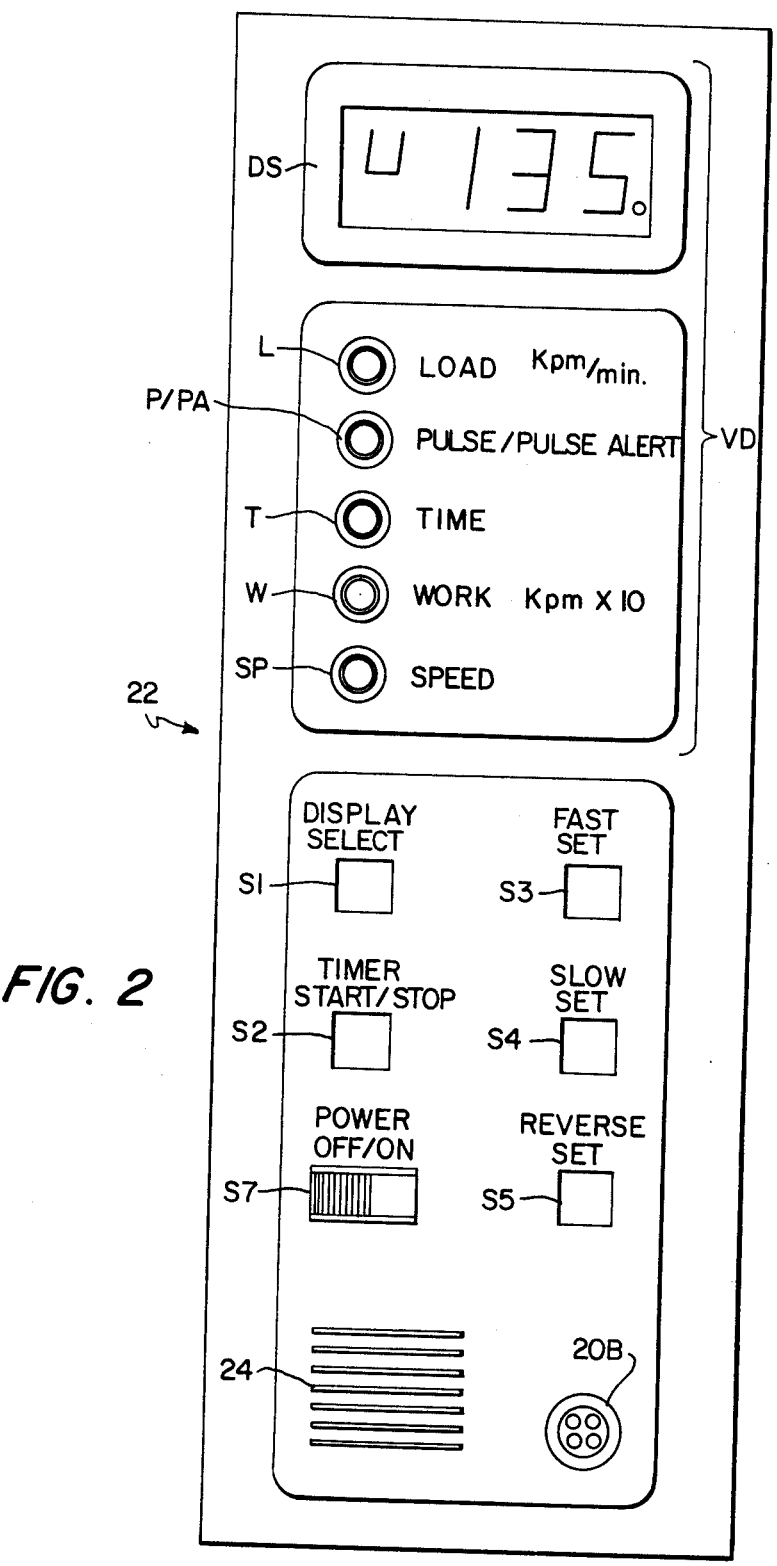
FIG. 2 is a plan view of the control panel and display format portion of the ergometric exerciser of FIG. 1.

With further reference to FIG. 1 and joint reference to FIG. 2, starting from the top of the control panel 22 the function and nature of the various indicators and controls thereon are as follows:

The digital display DS is a four digit display used to read out all numerical data required by the exercise unit 10, i.e. load, pulse rate, pulse limit, time and work.

The LED indicator lights L, P/PA, T, W and SP correspond to indications that the display DS and/or unit 10 are displaying and/or maintaining the respective parameters LOAD, PULSE/PULSE ALERT, TIME, WORK and SPEED. These LED indicators are seqentially lighted under the control of the DISPLAY SELECT switch S1. The numerical data in the DIGITAL DISPLAY DS then corresponds to the illuminated indicator except in the case of SPEED. The fifth INDICATOR LED SP (SPEED) is not controlled by the DISPLAY SELECT switch S1. This LED functions as a pedal speed indicator, glowing green when speed of the pedal 16A is above a minimum and flashing alternately red and green when that pedal speed is below that minimum.

The DIGITAL DISPLAY DS and LED INDICATORS L, P/PA, T, W and SP all comprise a visual display console VD.

The DISPLAY SELECT switch S1 is a pushbutton switch which is used to select what type of data is read out on the DIGITAL DISPLAY DS. Each activation of this switch S1 causes the top four LED INDICATOR lights L, P/PA, T and W to sequentially light in a top to bottom sequence with the displayed numerical data in the display DS corresponding to the illuminated LED switches. Note that the SPEED LED SP functions independently of the DISPLAY SELECT switch S1.

The control console 22 further includes a timer control switch S2 to be hereinafter more fully described FAST SET, SLOW SET and REVERSE SET switches S3, S4 and S5, respectively, are used to enter data into a microcomputer memory to be herinafter more fully described. These switches function in conjunction with the LOAD, PULSE/PULSE ALERT and TIME LED's, L, P/PA and T, respectively.

A remote display select switch S6 is provided on the handlebar assembly 14 to facilitate display selection during an exercise period as an alternative to the display select switch S1 positioned in the control panel 22.

A power ON/OFF switch S7 is also provided in the control panel 22 and will be more fully described hereinafter.

An audible transducer to be hereinafter more fully described, for providing a sonic alert or warning, is positioned behind a grillwork 24 on the control panel 22.

The control panel 22 is utilized to insert or enter control parameters into a microcomputer and to monitor the statistical parameters of an exercise routine. The basic functions of the control panel 22 are as follows:

Entering a Load Value

Using the DISPLAY SELECT pushbutton S1 turn ON the LOAD LED L, then press and hold the SLOW SET button S4 and the DIGITAL DISPLAY DS will increment 0, 300, 500, 700, 900, 1100, 1300, 1500, 1700, 1900, 2100 at about one reading per second. For safety the LOAD values do not roll back to zero. The REVERSE SET button S5 must be used to decrement the display DS through the above values at one reading per second. For setting load values only, the FAST SET button S3 operates identically to the SLOW SET button S4 incrementing the display DS at one reading per second. All load settings are in kpm per minute.

Setting a Pulse Limit Value

Using the DISPLAY SELECT buttons S1 turn ON the PULSE/PULSE ALERT LED P/PA. The FAST SET, SLOW SET and REVERSE SET pushbuttons S3, S4 and S5, can now be used to enter the pulse rate limit value. The FAST SET button S3 will increment the display DS at about a 10 reading per second rate for all functions except the load function. When any of these buttons S3, S4, S5 is first pushed, the display will show a "U" symbol in the left most position of the display DS to distinguish the displayed value from the user's actual pulse rate. When the exerciser 10 is first turned ON, the pulse limit value is automatically initialized to 0 (PULSE ALERT function disabled). In addition to this disabled setting, the pulse limit can be set to any value between 60 and 200 beats per minute. When not set to 0, the PULSE ALERT function is activated and the sonic alarm (to be herein after more fully described) will sound a "beeping" tone whenever the user's heart rate equals or exceeds the preset value. If the user's heart rate later falls below the preset value, the sonic alarm is deactivated. After setting the desired value, the next activation of the DISPLAY SELECT button S1 will remove the limit value and its "U" symbol and when the LED P/PA is again indicating the PULSE/PULSE ALERT function and DIGITAL DISPLAY DS will then be indicating pulse rate.

If the DIGITAL DISPLAY DS is not sequenced, the pulse limit value will remain displayed for only 30 seconds after the last of the SET buttons S3, S4, S5 is released. The DIGITAL DISPLAY DS then reverts to read out the user's pulse rate, not the pulse limit setting. This time-out feature is included as an additional safety precaution to preclude confusing the pulse limit setting with the user's actual pulse rate.

Presetting the Time

Using the DISPLAY SELECT button S1, turn ON the TIME LED T. If the exerciser 10 has just been turned ON, the DIGITAL DISPLAY DS will read zero. The FAST SET, SLOW SET and REVERSE SET buttons S3, S4 and S5 can now be used as described above to preset the internal exerciser timer (to be described hereinafter) to any value between 1:00 and 60:00 minutes in one minute increments. Only minute values can be preset, but when counting, the timer will decrement (or increment) seconds and minutes. The timer can now be started (and stopped) using the TIMER START/STOP button S2. When the timer is started, it will count down (decrement) to 0:00 and the automatically continue to count up. If allowed to count up indefinitely it will "roll over" to 0:00 and then automatically continue to count up. If allowed to count up indefinitely it will "roll over" to 0:00 after a count of 60:00 (i.e., elapsed time of one hour). When the timer is counting down the TIME LED T glows steadily, but when the timer is counting up the TIME LED T flashes. However, the flashing indication occurs only when the timer has not been selected for readout on the DIGITAL DISPLAY DS. If the timer has been selected for display, and the timer is in the count up mode, then the flashing signal will be overridden and the TIME LED T will glow steadily. The numerical display of the DIGITAL DISPLAY DS shows that the timer is counting up without need to refer to the flashing of the TIME LED T.

The timer function is completely independent of other exerciser functions. When the user starts to exercise he must start the timer using the TIMER START/STOP button S2. If the user stops exercising he may choose to stop the timer or let it run as he desires. The internal work computer (to be hereinafter described) is not affected by the user's operation of the timer.

In the event the timer has been preset and is decrementing without its count being displayed on the DIGITAL DISPLAY DS, the preset period will be indicated or completed when the count reaches zero since the counter will automatically commence incrementing and the TIME LED T will commence flashing in response thereto.

Thus, the different respective illumination modes (steady or flashing) of the LED T when the counter is decrementing or incrementing visually indicate to the user that the preset time period of a given exercise routine has been equalled or exceeded.

The POWER SWITCH Functions

The power ON/OFF switch S7 slides to the right to turn the exerciser 10 ON and to the left to turn it OFF. When the exerciser 10 is first turned ON by the power switch S7 it executes a routine to test the visual and aural indicators of the system. This routine causes the sonic alarm behind the grills 4 to sound for several seconds and simultaneously a 0 to be presented on the DIGITAL DISPLAY DS. Following this, the display DS will read 8888 and at the same time all five LED INDICATORS L, P/PA, T, W and SP will turn ON. Finally all test functions will be terminated and the LOAD function will automatically be selected for display as indicated by the glowing state of the LOAD LED L. Further, the displayed value of the load will be zero as indicated by a "0" on the DIGITAL DISPLAY DS.

Basic Functions and Components of the Exerciser System

Figure 3:
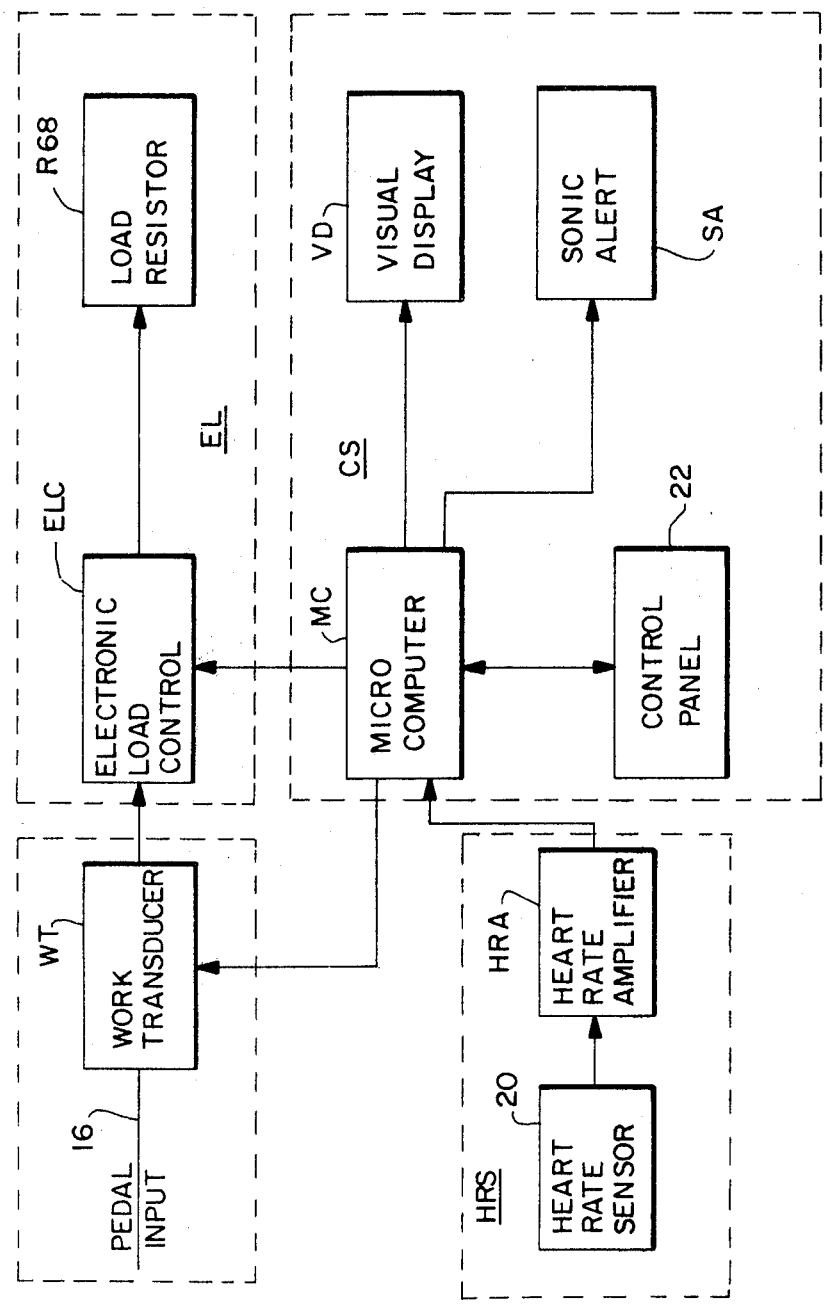
FIG. 3 is a general block diagram of the functional system components of the ergometric exerciser of the present invention.

Referring now to FIG. 3, the exerciser 10 of the present invention, which computes and displays the important parameters associated with a given ergometric exercise routine, is shown as including a work transducer WT, an electronic load EL, a heart rate sensing system HRS, and a computing system CS, the latter including a microcomputer MC, the visual display console VD, control panel 22 and a sonic alert module SA.

The work transducer WT is an alternator which converts mechanical work at its input shaft (driven by pedal input 16) into electrical work delivered to a load resistor R68. An electronic load control EL is used to regulate and control the electrical output of the alternator to make its output constant above a minimum speed of the pedal assembly 16. These circuits also select the electrical loading in predetermined steps under control of the microcomputer MC to vary the exercise work performed by the user. The heart rate sensing system HRS uses an optical pulse rate sensor 20 (FIG. 1) attached to an ear lobe of the user to detect the pulse of the user and generate a representative pulse signal. This signal is conditioned by the heart rate amplifier HRA of the heart rate system HRS before processing by the microcomputer MC to extract average heart rate information. Finally, the microcomputer MC controls and supervises the entire exerciser 10 and interfaces with the user via the control panel 22 and visual/aural displays VD and SA.

The Work Transducer WT and Electronic Load EL

Figure 4:
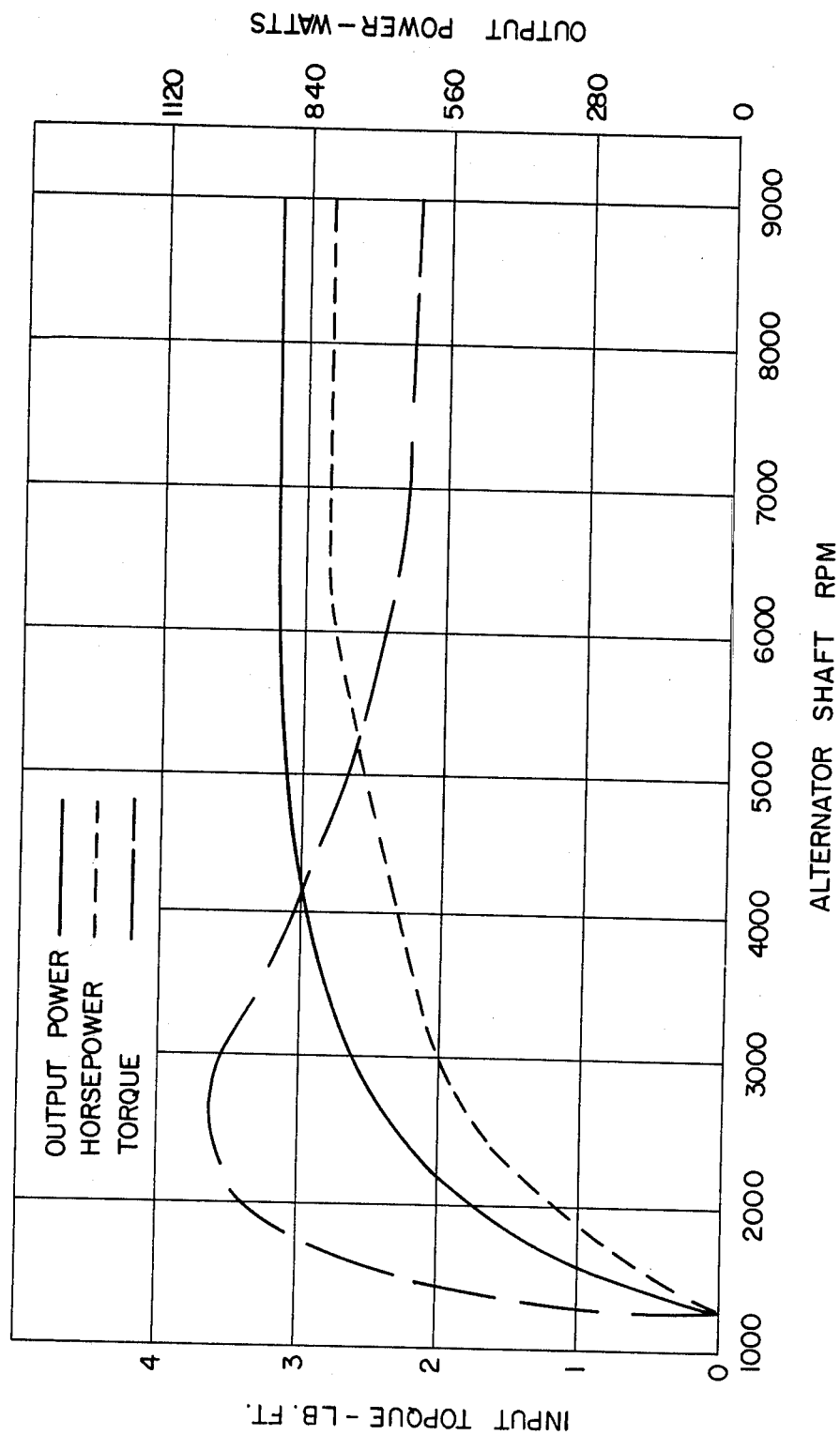
FIG. 4 is a graph plotting output power, horse power, and torque versus the alternator shaft RPMs of the work transducer alternator of the present invention.
Figure 5:
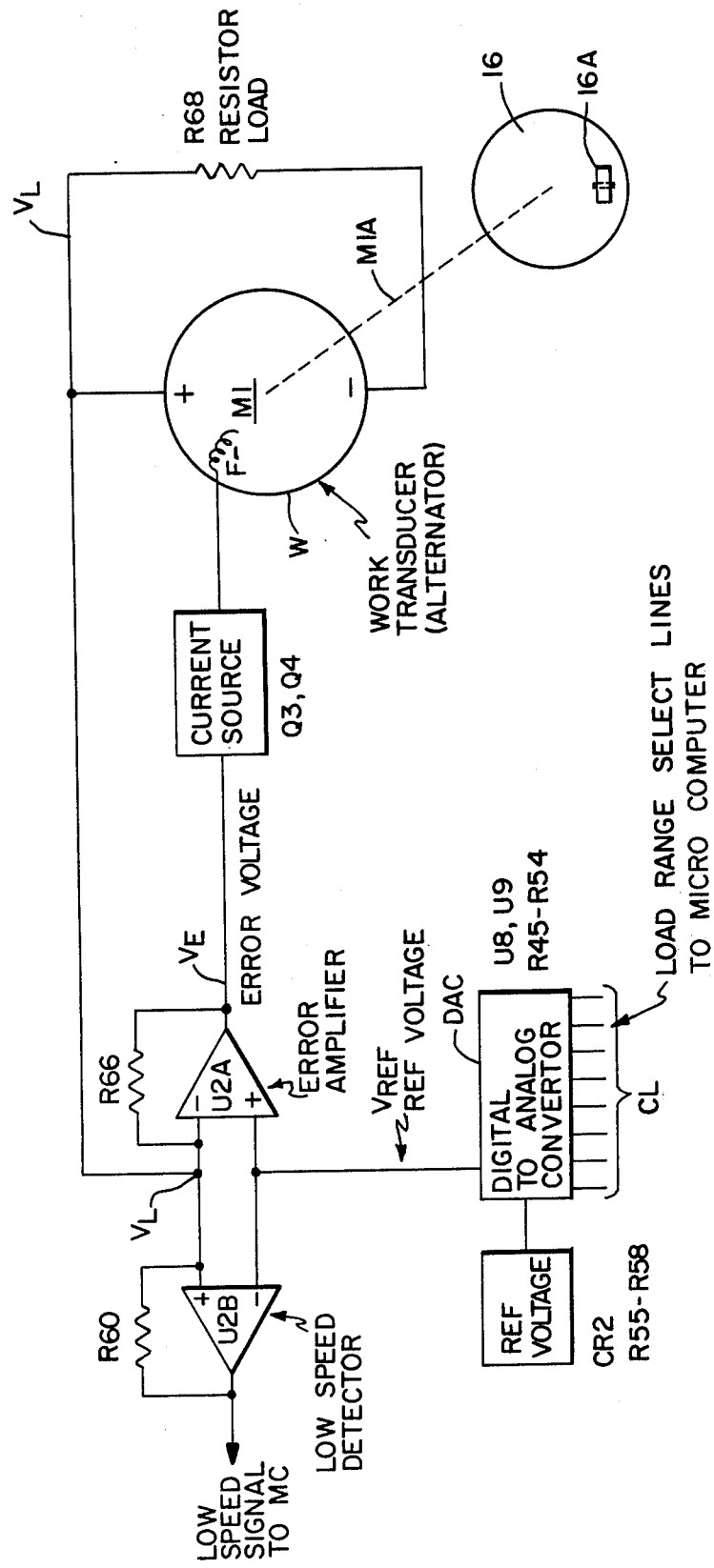
FIG. 5 is a detailed block diagram of the electronic load circuit including the work transducing alternator of the present invention.

Referring now to FIGS. 4 and 5, the work transducer WT comprises a standard automotive type alternator M1 driven in relation by a rotary coupling (input shaft) MIA from the pedal assembly 16.

FIG. 4 illustrates the alternator characteristics defining the conversion of mechanical energy into electrical energy, that is shaft rotation and input torque are converted into electrical power (WATTS). FIG. 4 shows that as the power output of the alternator M1 increases the required input torque increases, or as the output power decreases input torque decreases. By controlling the output power of the alternator M1 the amount of input torque or input horsepower required from the pedal assembly 16 for a given amount of work can be changed.

In addition to the mechanical energy at the alternator input MIA, the field winding F must be excited by a small D.C. current (100-2000 MA). If the alternator input (shaft) speed and loading at the output of the alternator are constant, the amount of output power from the alternator M1 can be made to vary by changing the amount of current applied to the field winding F. The greater the field current the greater the output power. Therefore, the amount of work being input at the shaft of the alternator can be controlled or changed by varying the field current. This is the principle used to make the alternator M1 function as a work transducer WT.

All major parts of the circuit that regulates and controls the amount of work done at the pedals 16A by a user are shown in FIG. 5. This circuit is basically a variable voltage regulator circuit comprised of an error amplifier U2A, a digital to analog converter DAC, the alternator M1 and load resistor R68. The error amplifier U2A has two inputs: one a reference voltage REF generated by the digital to analog converter DAC and the other, the output of the voltage $V_L$ alternator M1. The error amplifier U2A causes an error voltage $V_E$ to be generated at its output terminal proportional to the difference of the voltages that are applied at its input terminals as shown in the equation below:

ERROR VOLTAGE=([REFERENCE VOLTAGE]−[ALTERNATOR OUTPUT])×100

This error voltage is then converted into a current by a current source Q3, Q4 and applied to the field winding F of the alternator M1. Therefore, the work regulation circuit causes a constant voltage $V_L$ to be generated across the load resistor R68, equal to the reference voltage $V_{Ref}$ generated by the digital to analog converter.

A feedback resistor R66 is connected between the said other ($V_L$) input and the output ($V_E$) terminals of the error amplifier U2A.

The microcomputer MC (FIG. 3) controls the digital to analog converter DAC by placing a high logic level onto one of the 11 control lines CL schematically shown. As each LOAD range is selected a different reference voltage $V_{Ref}$ will be output from the digital to analog converter DAC. If the minimum speed required for the alternator M1 to generate the required power is maintained, the voltage $V_L$ across load resistor R68 will equal the reference voltage $V_{Ref}$ generated by the digital to analog converter DAC. Thus the work input will be regulated as long as the speed at the alternator shaft is above a minimum value.

The load regulation circuit also signals the microcomputer MC when the shaft speed of the alternator M1 is too low to generate the required load voltage $V_L$. This function is performed by the low speed comparator U2B. The low speed comparator U2B has two inputs, one the reference voltage $V_{Ref}$ generated by the digital to analog converter DAC, the other from the voltage $V_L$ generated across the load resistor R68 by the alternator M1. Whenever the voltage output $V_L$ from the alternator M1 falls below the reference voltage $V_{Ref}$ generated by the digital to analog converter DAC, the output of the low speed comparator U2B changes states to signal the microcomputer MC that the amount of work being input at the pedals 16A is no longer being regulated.

By way of example, reference is made to Table 1 below, which shows the LOAD ranges that can be selected and the minimum speed required at the alternator shaft MIA and pedals 16A to maintain work regulation, and the sources and amount of error on each LOAD range. Note that the error amounts shown in Table 1 are based on calculated data taken from a sampling of several typical alternators.

TABLE 1

| | ERGOMETRIC EXERCISER 10 LOADING CHARACTERISTICS AT ALTERNATOR SHAFT MIA | | | | |
|---|---|---|---|---|---|
| RANGE KPM/MIN | SPEED AT ALTERNATOR TO REGULATE LOAD | SPEED AT PEDAL TO REGULATE LOAD | ALTTERNATOR-ALTERNATOR VARIATION | SPEED VARIATION ERROR | TOTAL LOADING ERROR |
| 300 | 600 | 28 | ±10% | ±15% | ±25% |
| 500 | 800 | 36 | ±10% | ±10% | ±20% |
| 700 | 900 | 40 | ±10% | ±10% | ±20% |
| 900 | 900 | 40 | ±10% | ±10% | ±20% |
| 1100 | 1000 | 45 | ±10% | ±10% | ±20% |
| 1300 | 1100 | 50 | ±10% | ±10% | ±20% |
| 1500 | 1300 | 59 | ±10% | ±10% | ±20% |
| 1700 | 1400 | 63 | ±10% | ±10% | ±20% |
| 1900 | 1500 | 68 | ±10% | ±10% | ±20% |
| 2100 | 1900 | 86 | ±10% | ±10% | ≅20% |

The error amplifiers U2A and U2B are portions of commercially available IC amplifier chips known as LM 2902 Quad Op Amps of National Semiconductor.

The digital-to-analog converter DAC is comprised of two IC chips known as CA3081 General Purpose High Current N-P-N Transistor arrays of RCA.

The Heart Rate Amplifier and Sensor System HRS

Figure 6:
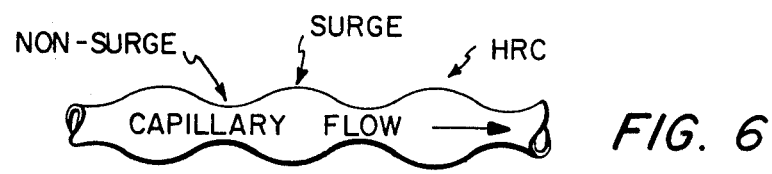
FIG. 6 is a diagrammatic illustration of the pulsating capillary flow of blood through a vein in the users ear lobe.
Figure 7:
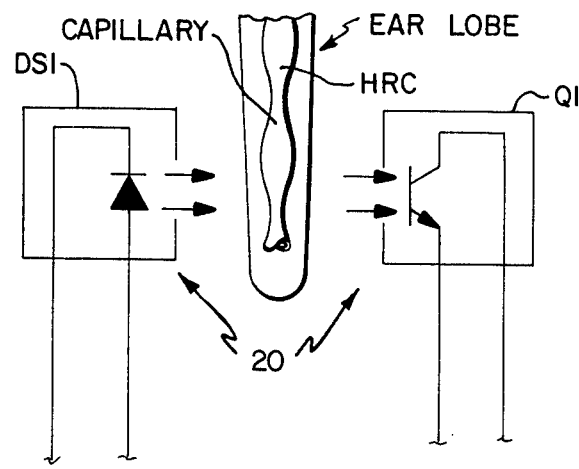
FIG. 7 is a diagrammatic view of an ear clip pulse sensor for use with the pulse rate sensor mode of operation of the ergometric exerciser of the present invention.

The heart rate sensor 20 is designed to convert pulse beats or surges in the capillary blood flow of the ear lobe into electrical pulses to be amplified and conditioned by the heart rate amplifier HRA. Referring to FIGS. 6 and 7, these blood surges are represented as expanded sections of a capillary HRC alternating with unexpanded non-surge areas.

The heart rate sensor 20 is an ear clip which incorporates two devices DS1 and Q1 which recognize and measure the variations between each surge and non-surge of the user's pulse. One device is an infrared light emitting diode DS1 which projects a small beam of infrared energy into the capillaries HRC of the user's ear lobe. The other device is a phototransistor Q1 which detects the amount of infrared energy transmitted through the ear lobe from the infrared emitting diode DS1 between each surge and non-surge and converts it into a low level elecrical signal of about 15 mv. peak-to-peak at the emitter terminal of the phototransistor Q1.

Figure 8:
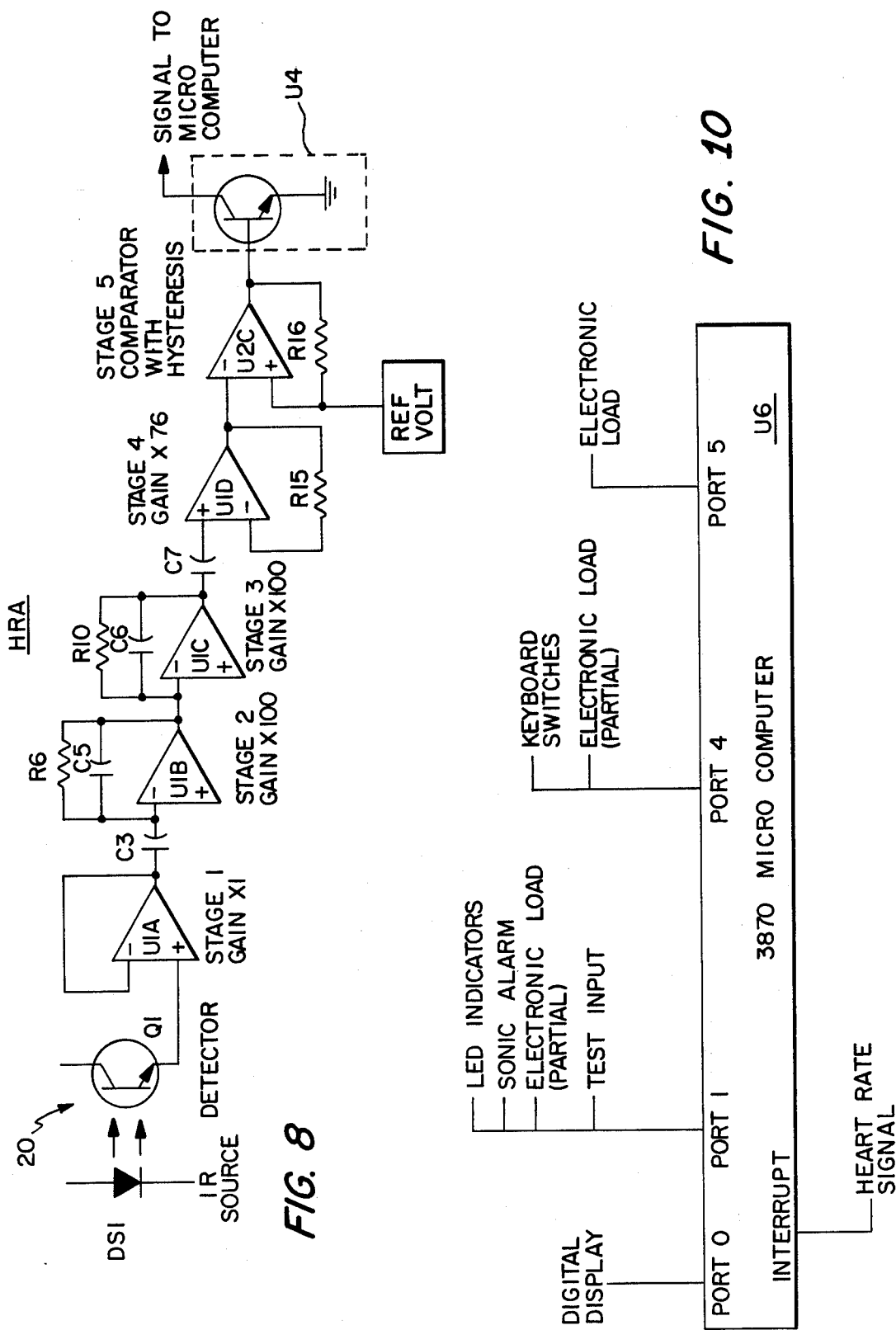
FIG. 8 is a detailed schematic diagram of a heart rate amplifier coupled to the pulse rate sensor of the present invention.

Since the signal received from the phototransistor Q1 is low in amplitude, it must be amplified and conditioned before being applied to the input of the microcomputer MC. Referring now to FIG. 8, the major parts of the heart rate amplifier HRA are shown. The signal from the phototransistor Q1 of the heart rate sensor 20 is applied to the input of a first amplifier stage V1A which is connected as a voltage follower stage to provide impedance matching (buffering) between the phototransistor Q1 and the other amplifier stages of the heart rate amplifer HRA. The output of the voltage follower U1A is then A.C. coupled through a capacitor C3 into amplifier stages U1B and U1C, which provide a voltage gain of about 100 for each stage and filtering through respective parallel RC networks C5R6 nad C6R10 to remove all high frequency signal components. The amplified signal from the third stage U1C is A.C. coupled through capacitor C7 into the fourth stage U1D which has a gain of about 76 and provides a signal of about 4 volts peak-to-peak at its output.

The signal from the fourth stage U1D is next converted into a signal that is compatible with the microcomputer MC by applying it to a fifth stage U2C, which is a voltage comparator with hysteresis. A suitable reference voltage for the comparator U2C is applied to the positive input of the comparator stage U2C. Since the comparator U2C operates from an unregulated power supply to be hereinafter described, it is necessary to level shift the output of the comparator U2C to a 0-5 volt level compatible with the microcomputer MC. This is done by a transistor section of IC package U4 which will be fully defined in connection with FIG. 12. The level shifted signal is applied directly to an appropriate input port of the microcomputer MC for processing.

The stages U1A-U1D are all part of a common IC chip U1 known as an LM 2902 Quad Op Amps of National Semiconductor.

The fifth stage U2C is part of the IC chip U2 already defined in reference to FIGS. 4 and 5 as a similar LM 2902 including stages U2A and U2B.

Other details of the schematic of FIG. 8 will be fully described in reference to FIG. 12.

The Microcomputer MC

The microcomputer MC controls and supervises the entire exerciser 10 and interfaces with the user via the control panel 22, visual displays VD and aural indicator. The microcomputer MC keeps time, computes data, makes decisions and provides controls for the input/output devices used in the exerciser 10.

Figure 9:
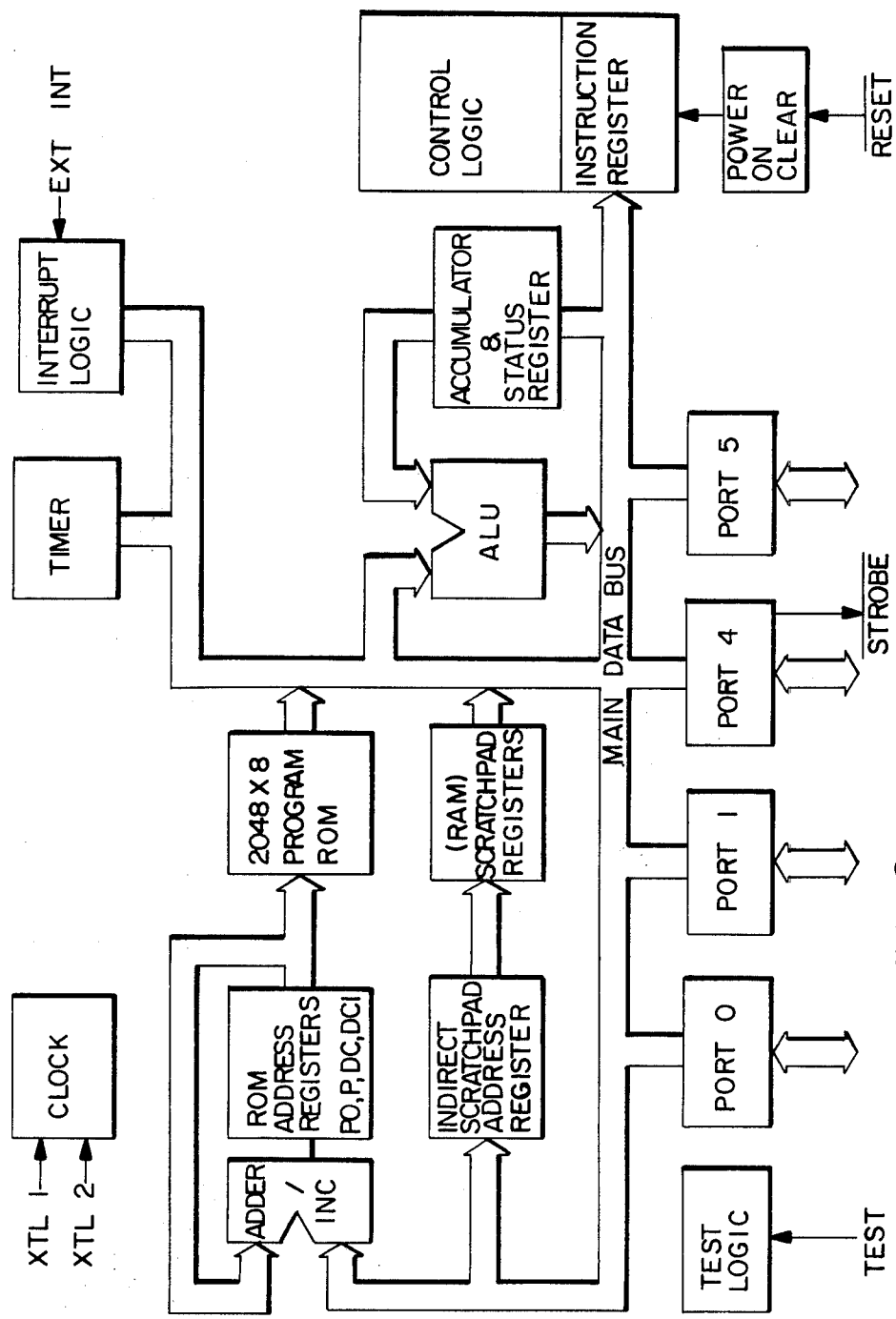
FIG. 9 is a detailed block diagram of the commercially available microcomputer utilized with the ergometric exerciser of the present invention.

Referring to FIG. 9, the internal block diagram of the microcomputer MC that is used in the exerciser 10 is shown. The microcomputer MC is preferably a commerically available type 3870, a complete 8 bit microcomputer on a single MOS integrated circuit chip. Utilizing ion-implanted, N-channel silicon-gate technology and advanced circuit design techniques, this 3870 microcomputer contains 2048 bytes of mask programmable ROM, 64 bytes of scratch pad RAM, 32 input-/output lines, programmable timer and external interrupt and is crystal controlled. The 3870 microcomputer is manufactured by Fairchild Semiconductor, Motorola and Mostek.

The 3870 is a complete processor system on a single chip and does not require any additional circuits aside from the power supply. This single chip U6 will be further described in FIG. 12 and is fully disclosed in the attached Appendix A.

Figure 11:
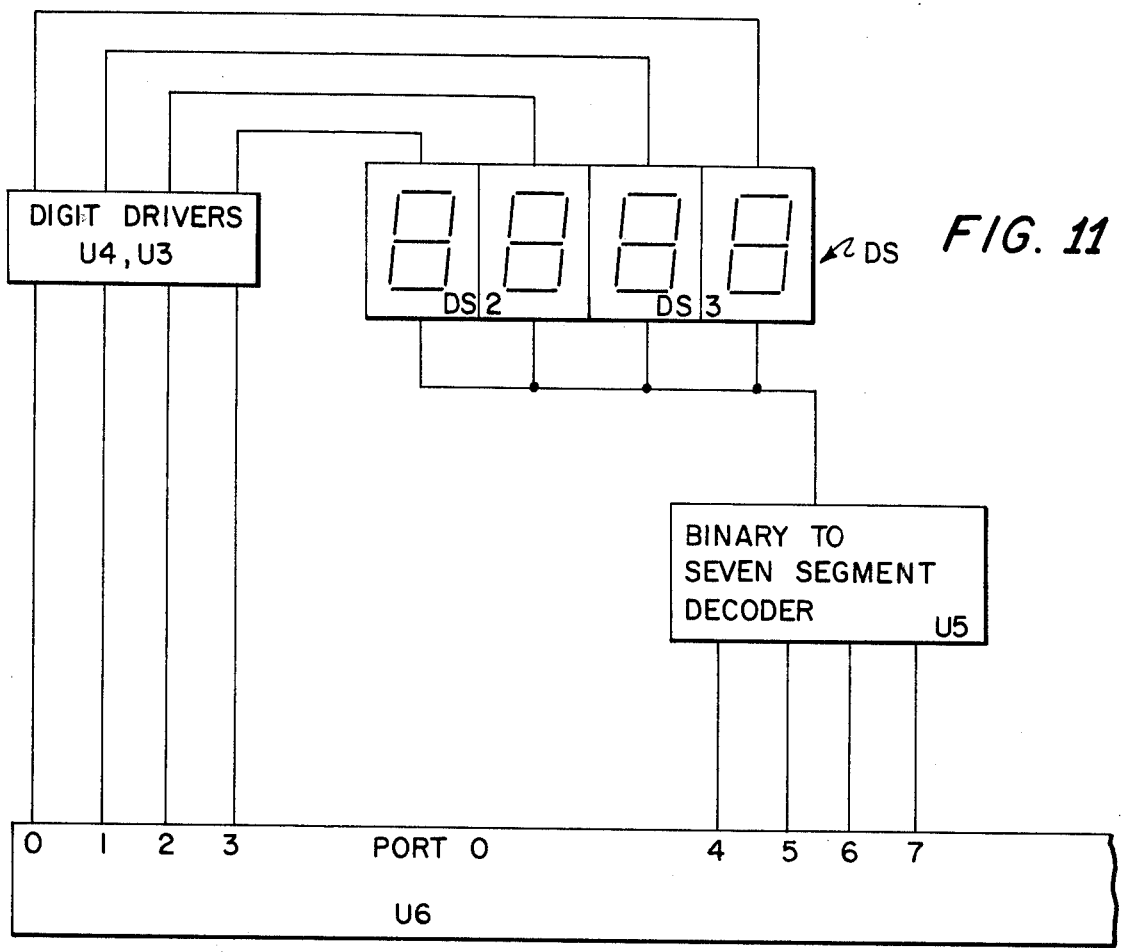
FIG. 11 is a diagrammatic view illustrating the interfacing of the digital display of the present invention with the microcomputer of FIG. 9.

The microcomputer communicates with the operator and the input/ouput devices thought its four I/O ports PORT 0, PORT 1, PORT 4 and PORT 5. Each I/O port has 8 lines which can be programmed by software to be an input line or output line. Each I/O port and the devices that are respectively controlled thereby are schematically shown in FIG. 10 to which reference is now made. I/O PORT 0 controls the four digit digital display DS. The display DS is time multiplexed in response to the activation of the display select switch S1 previously described. As shown in FIG. 11, lines 0-3 are the digit select lines and lines 4-7 are the data lines. The four data lines output the binary equivalent of the data that is to be displayed. The binary data is converted by an IC U5 to the seven segment code that is required to drive the display digits. Since the display DS is multiplexed, the microcomputer MC outputs the proper binary data on lines 4-7 of PORT 0 and then selects the proper digit driver transistor in IC U3 and/or U4 to enable the digit that the data is to be displayed on. Each digit of the display DS is refreshed or selected for 1 msec. out of each 4 msec. period. The digit display DS is comprised of a pair of two-digit display modules DS2 and DS3 which are commercially available display modules FND 6710 Dual Digit Numeric LED displays of Fairchild.

FIG. 10 further shows I/O PORT 1 interfaced to the LED indicators, the sonic alarm, the electronic load and the test input line. As best shown in FIG. 12C, lines 0-4 control each of the LED indicators L, P/PA, T, W and SP on the control panel 22, line 5 enables the sonic alarm SA, line 6 has been reserved as a test input to tell the microcomputer MC to go into a self-test mode, and line 7 is a signal from the electronic load EL indicating that the load is not regulated because of low speed at the alternator shaft M1A. I/O PORT 4 connectes the microcomputer MC to the keyboard switches S1-S7 on the control panel 22 and to some of the interface signals of the electronic load EL. As best shown in FIG. 12D, lines 0-4 interface the keyboard switches S1-S7 and lines 5-7 drive some of the control lines which select ranges on the electronic load EL. I/O PORT 5, lines 0–7, are used to select the remaining ranges on the electronic load EL as best shown in FIGS. 12D and 12E.

In addition to these 4 I/O PORTS, the microcomputer MC has an external interrupt input INT EXT. This line (PIN 38, U6 IC FIGS. 12) is interfaced to the output of the heart rate amplifier circuit HRA via the ICU4. The microcomputer MC uses this line to measure the time interval between heart beats and executes a software routine to compute the heart rate value from the measured time interval.

Since many functions in the exerciser 10 require time interval measurements of high accuracy, a crystal time base with high accuracy is used. The crystal Y1 used is a standard TV color burst crystal (frequency 3.579545 MHZ); this components is very accurate (0.002%), although inexpensive because it is in high volume production for the TV industry. From this crystal clock Y1 the microcomputer MC, using its internal prescaler and 8 bit timer, generates an accurate 1 msec. timing signal which is then used by the software to control all exerciser timing functions.

A complete software printout of the exerciser 10 is annexed hereto as Appendix B.

A complete set of flow chart diagrams corresponsing to the software printout are presented in FIGS. 13 through 27.

The Software

The software of the microcomputer MC determines the personality of the exerciser 10. For the microcomputer MC to perform any specified operation, it must receive and process a sequence of instructions. The sequence may be very long, numbering into the thousands of instructions. This sequence of instructions that can be taken as an overall unit is called the program or software. The software controls all operations that the microcomputer MC performs.

The software of the exerciser 10 resides in the 2048 bytes of mask programmed ROM (Read Only Memory) inside the microcomputer MC chip, itself. The prefered embodiment of exerciser software requires about 1400 bytes of the ROM.

The major routines of the software are the initialization routine, timer update routine, main loop routine, heart rate computation routine and self-test routine. The initialization routine is only executed during a power-up sequence. The initialization routine clears all registers and sets up all system constants. The timer routine is executed each time the internal timer of the microcomputer causes an interrupt. This interrupt occurs at a 1 msec. rate. The timer routine updates all system timing functions each time the interrupt is received. The main loop routine supervises all I/O devices such as the control panel 22, display VD, sonic alert SA and electronic load EL. The main loop routine also scans the external interrupt input line INT EXT to test if the output of the heart rate amplifier HRA has changed state. When this output changes state, the main loop routine will call up the heart rate computation routine. Once the heart rate routine is called, it will compute the heart rate in beats per minute based on the time interval measured between heart beats.

The heart rate routine uses a special algorithm to allow it to disregard any beats that are not in the 40–200 beat per minute range. In addition, this algorithm has been designed to "average out" the beat-to-beat variations exhibited by a normal person because they are confusing and not as meaningful as a "smoothed" or "averaged" value. This algorithm further allows the displayed heart rate to change by only ±1 digit for each beat. For example, if the heart rate is being displayed as 70 and the next beat is computed as being 65, the display will be undated as 69. As long as additional beats are computed as lower than the displayed value, the display will be decremented by 1 count. Conversely, if the actual computed value is greater than the displayed value, the display will be incremented by 1 count. Finally, if no heart beats are detected for a 15 second period, the heart rate display is reset to zero. The software for the heart rate routine has been carefully designed to provide a heart rate readout which is as "fool-proof" as possible.

The self-test routine will only be used during final test at manufacture or when the electronics package requires factory service. The self-test routine can only be executed when a special test-set is connected to the electronics package. The self-test routine will start a test sequence that will automatically test most electronic functions in the exerciser.

Circuit Details of the Exerciser 10

Figure 12A:
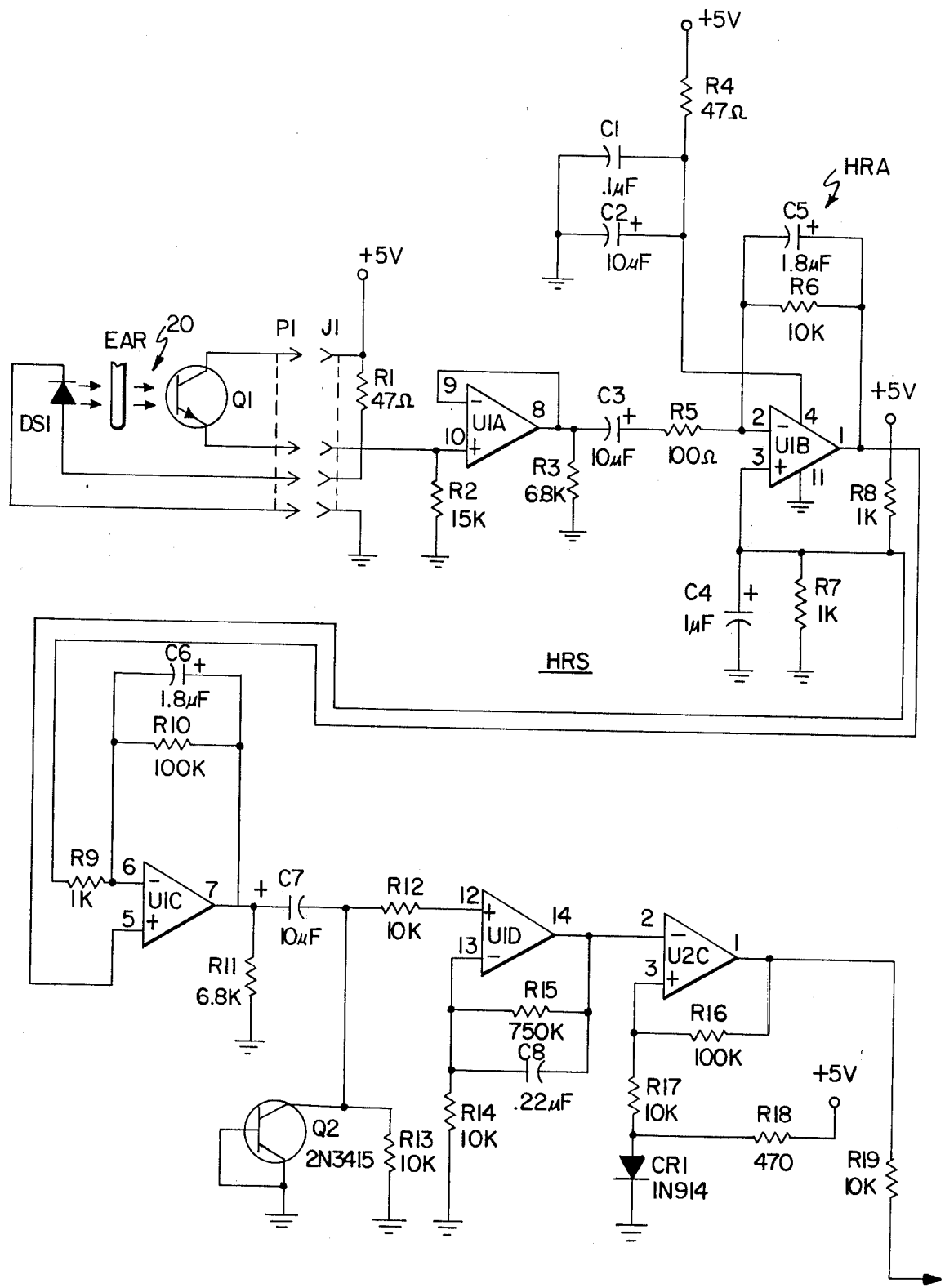
Figure 12B:
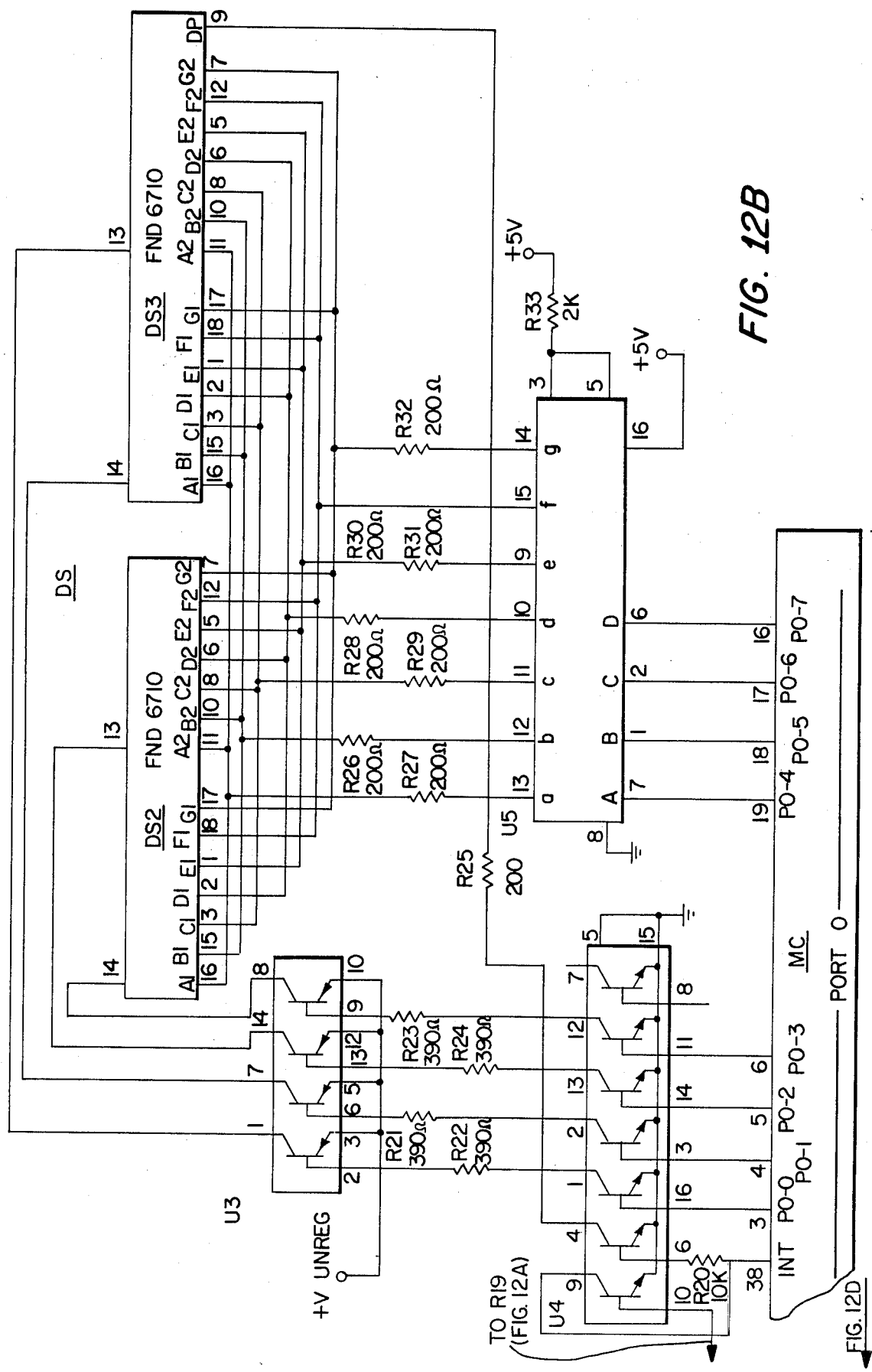
Figure 12C:
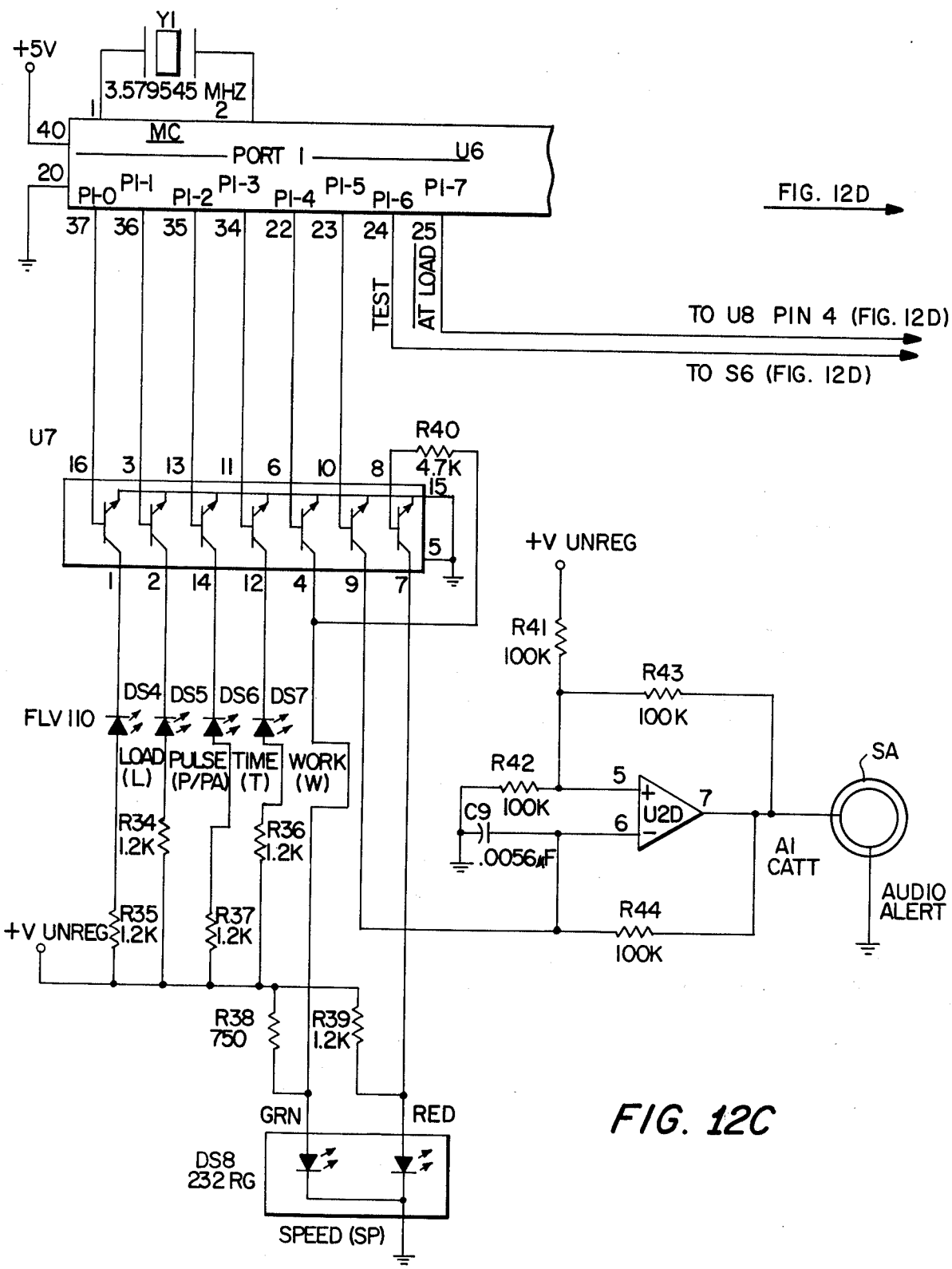
Figure 12D:
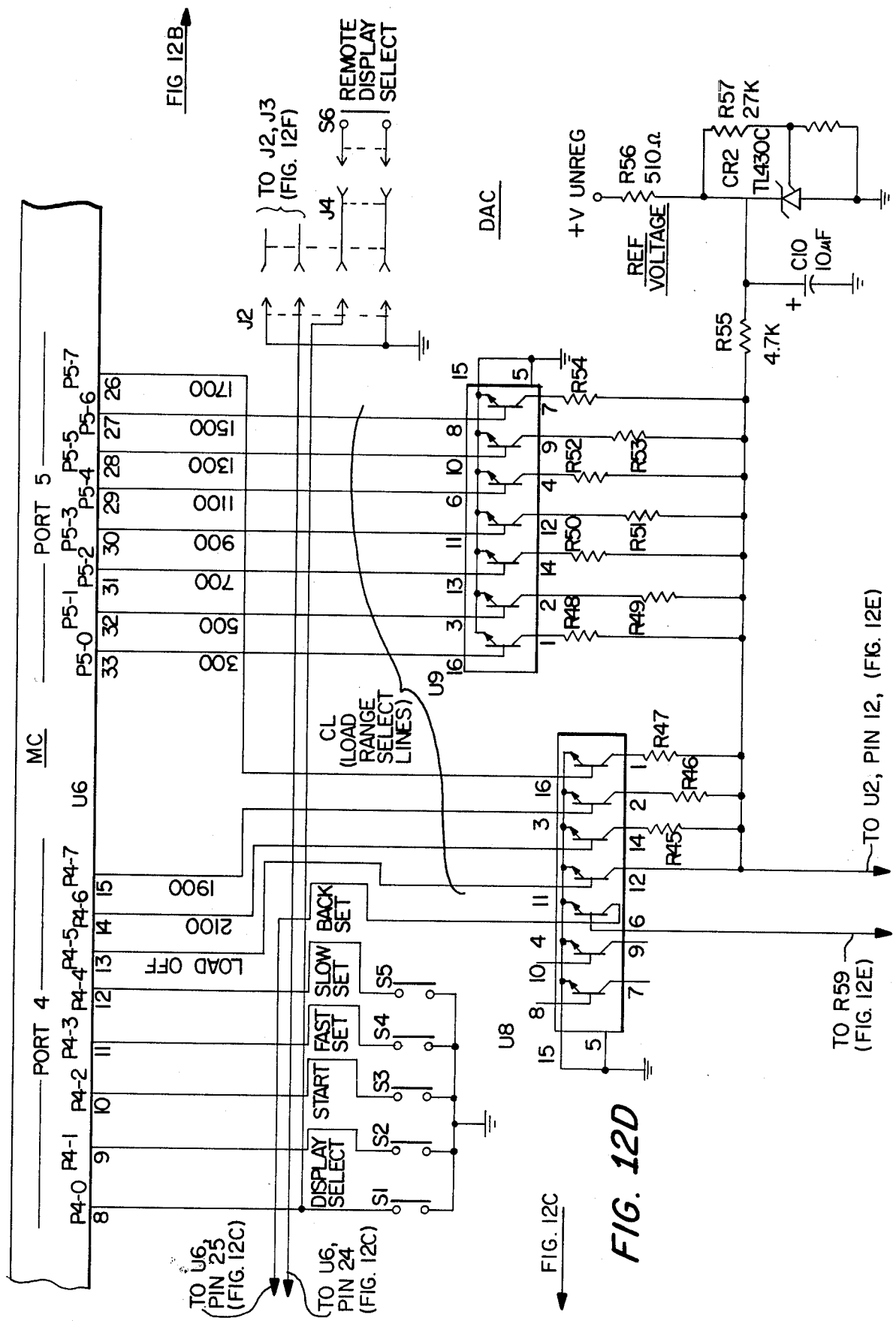
Figure 12E:
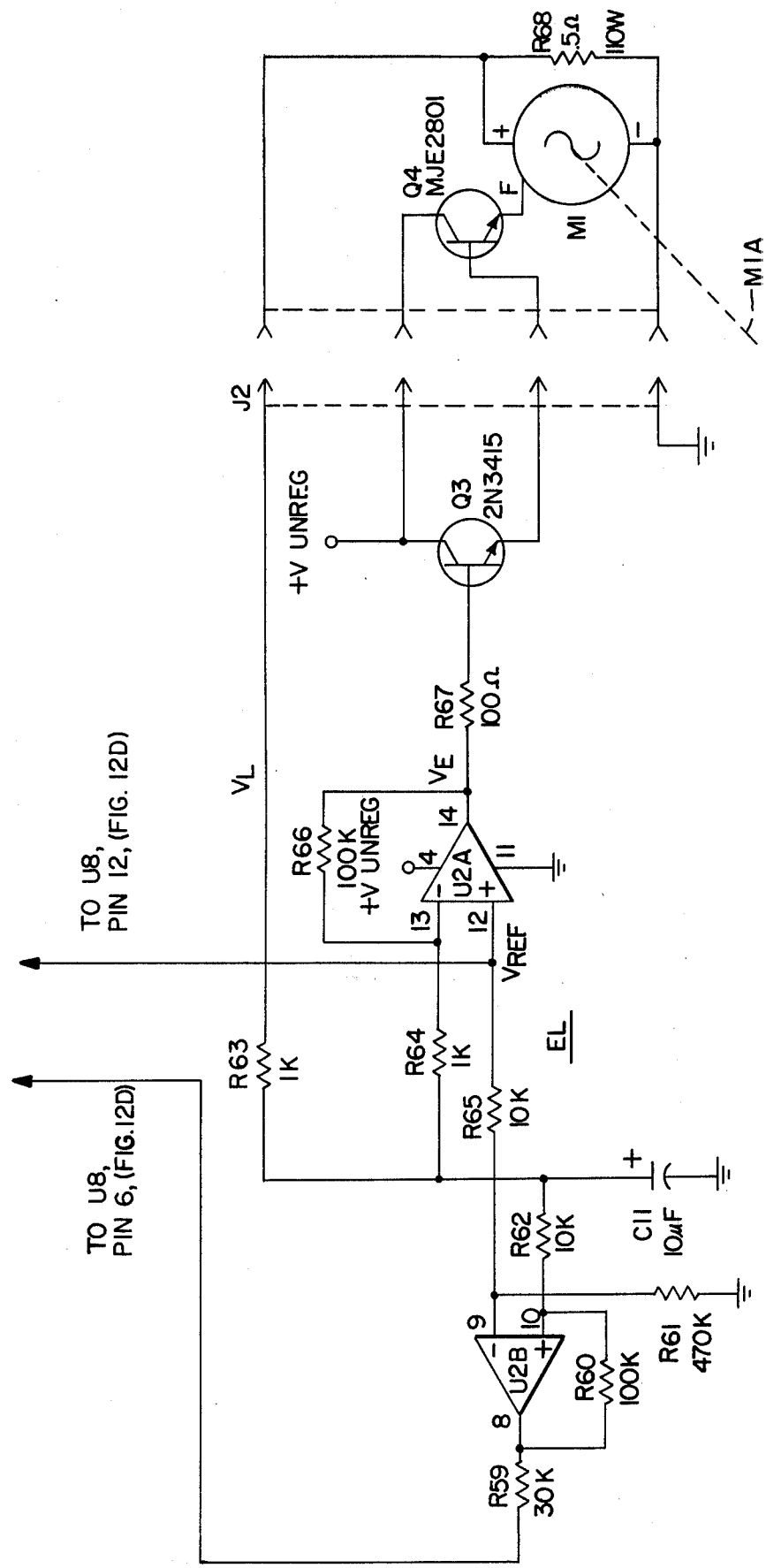
Figures 13, 14:
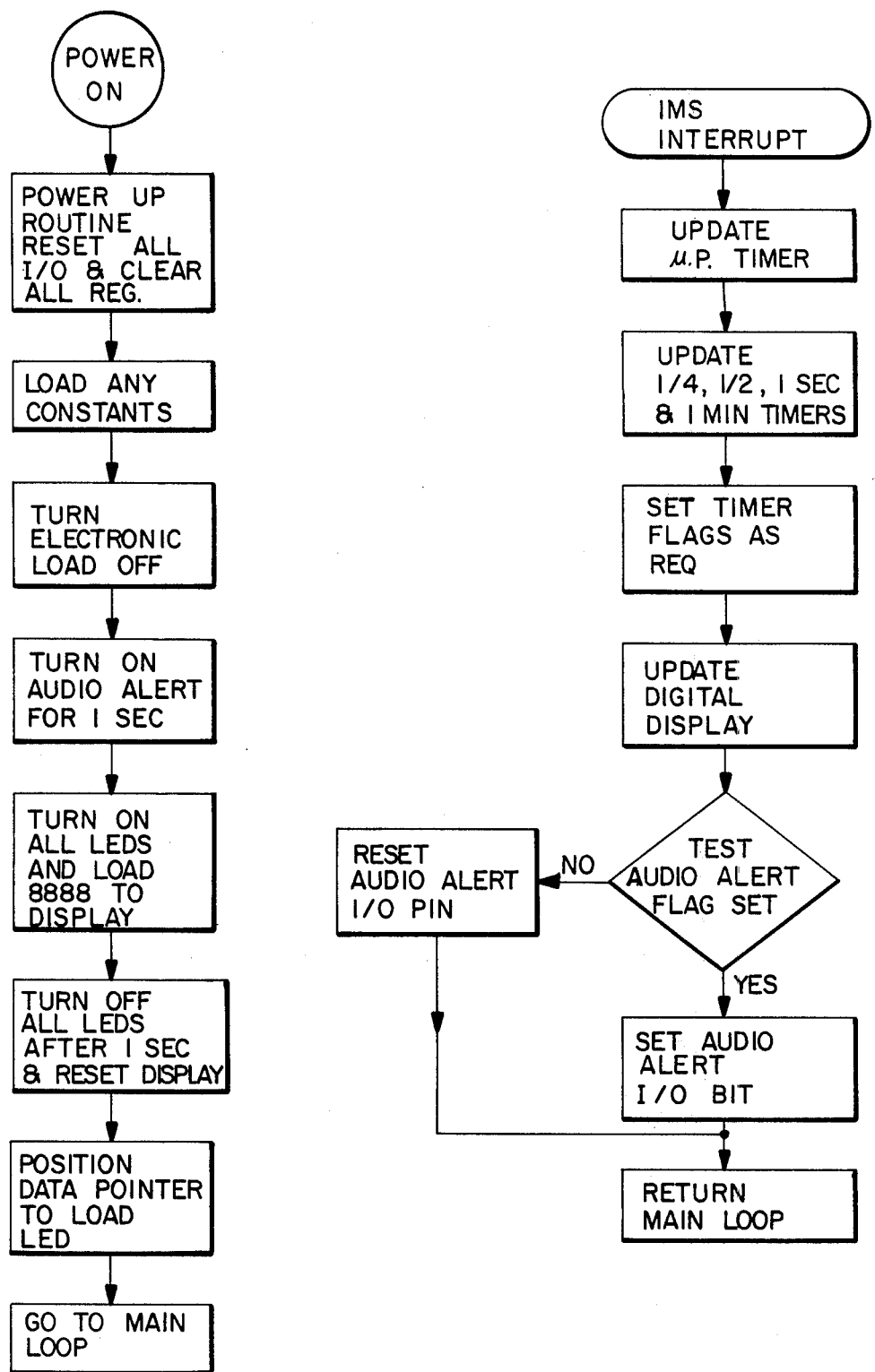
FIGS. 13 to 27 comprise the software program flow chart for operating the microprocessor of FIG. 9 to perform desired functions in accordance with the present invention.
Figure 15:
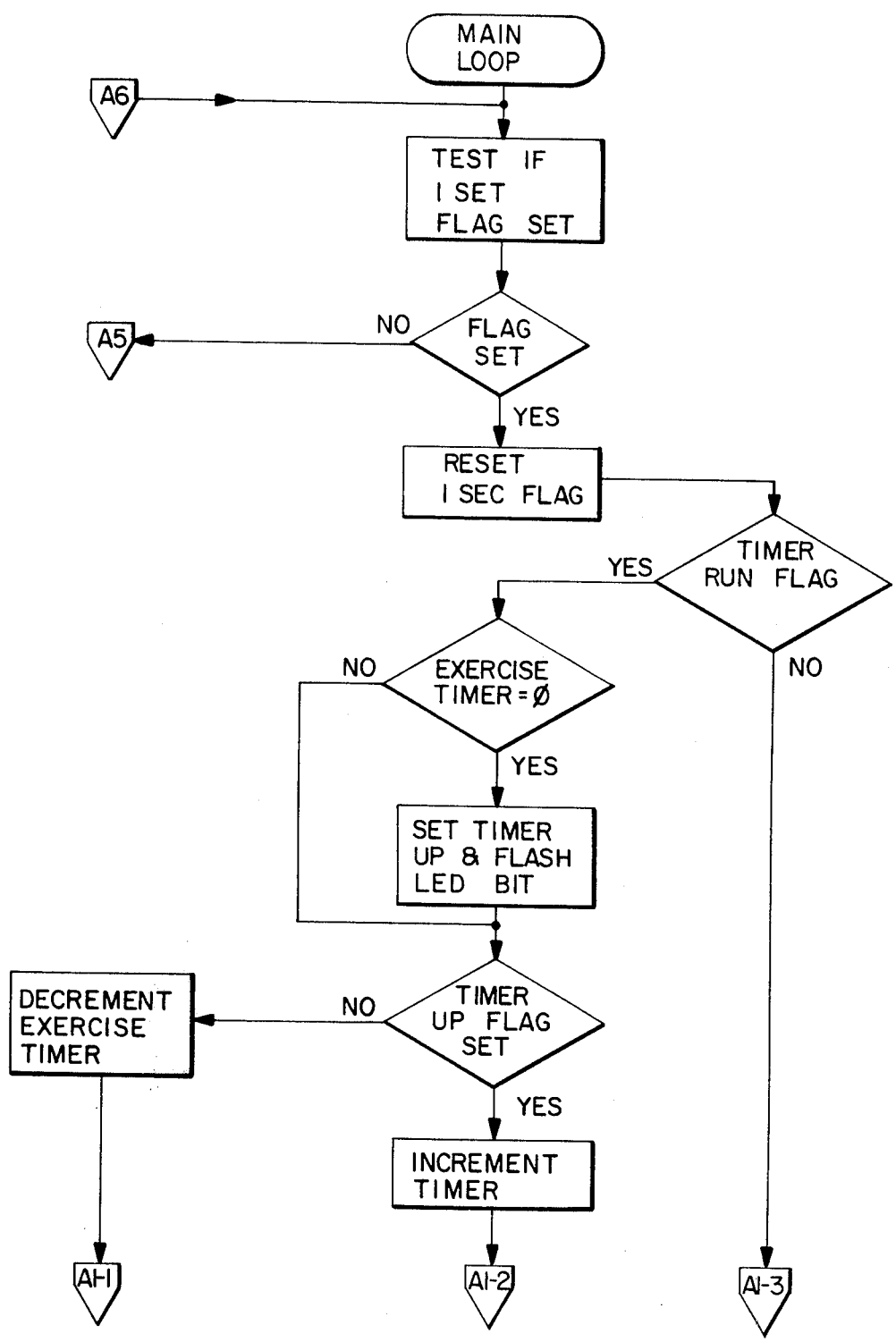
Figure 16:
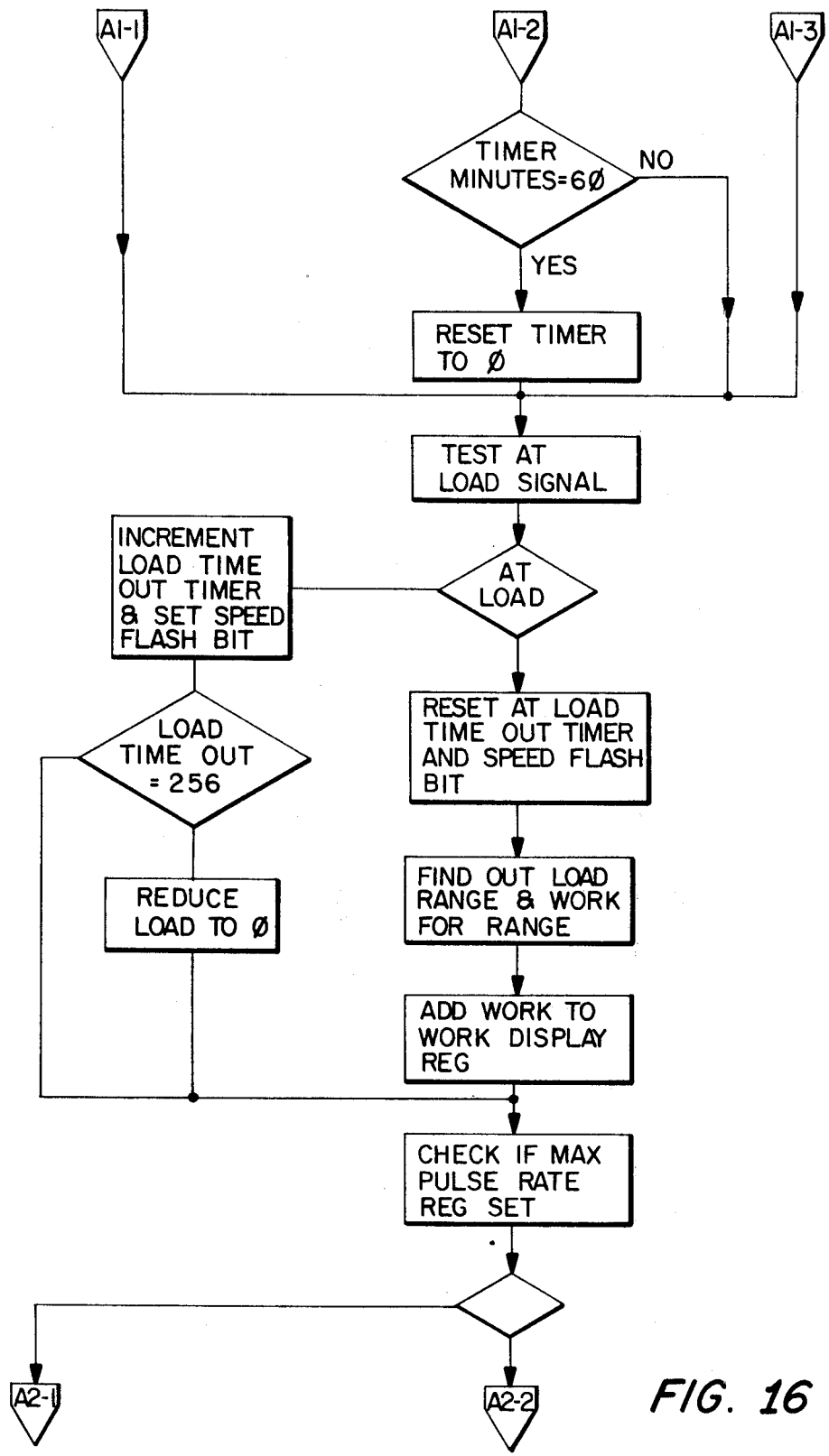
Figure 17:
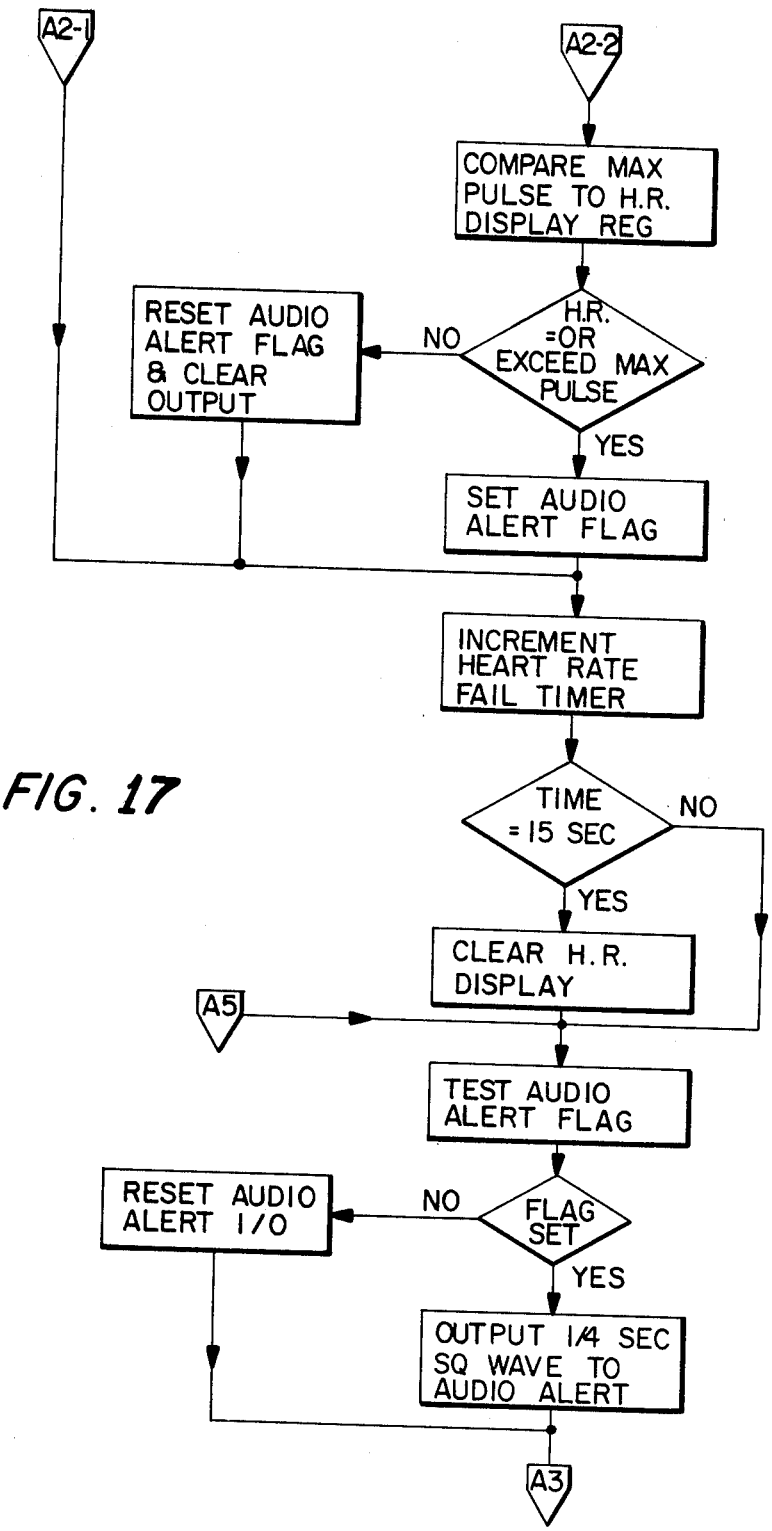
Figure 18:
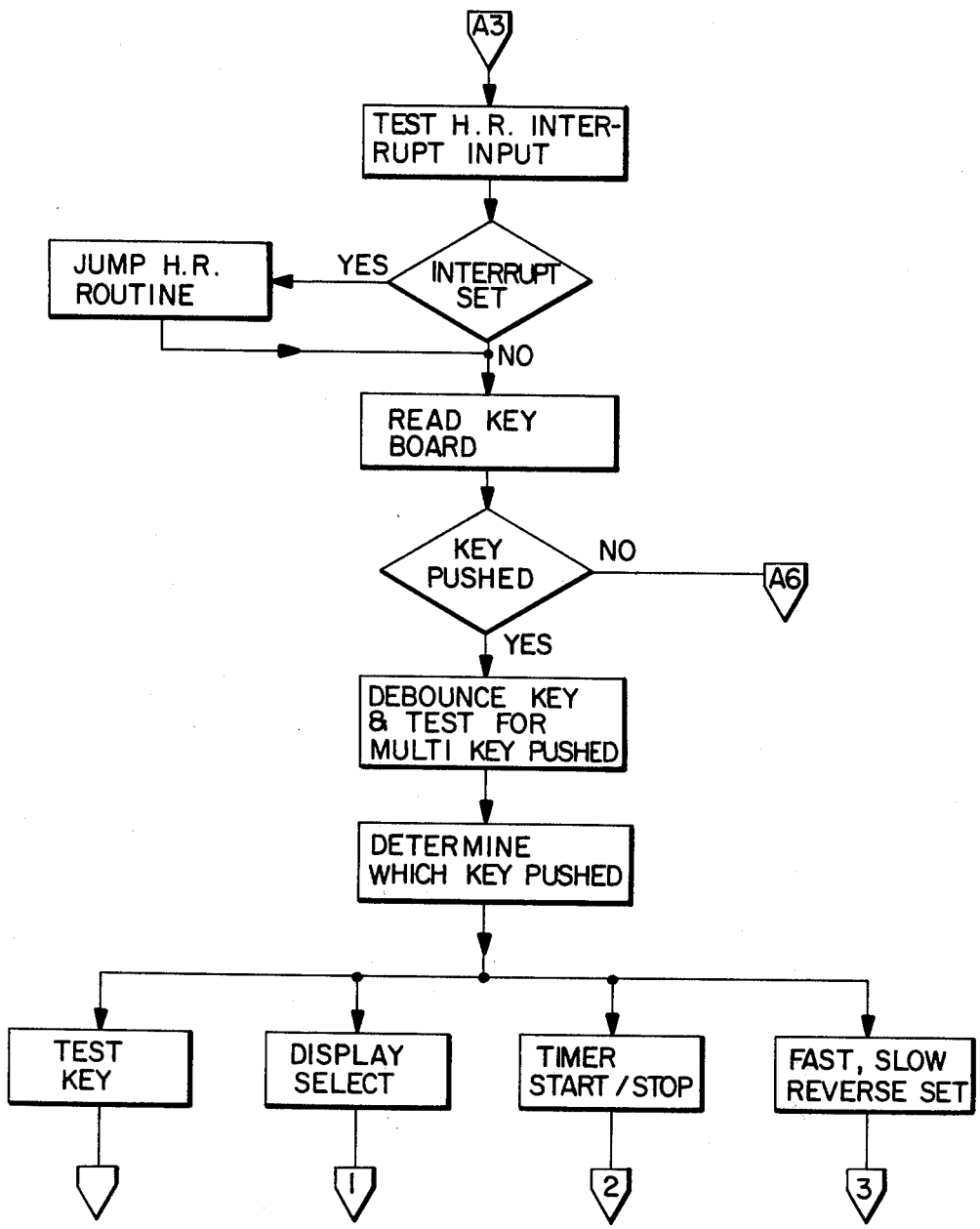
Figure 19:
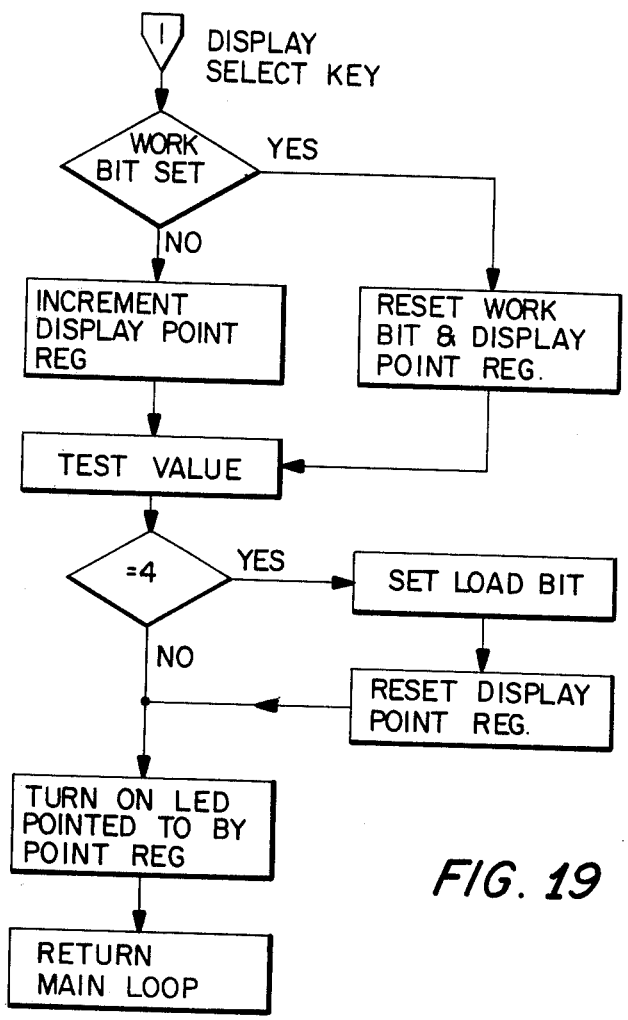
Figure 20:
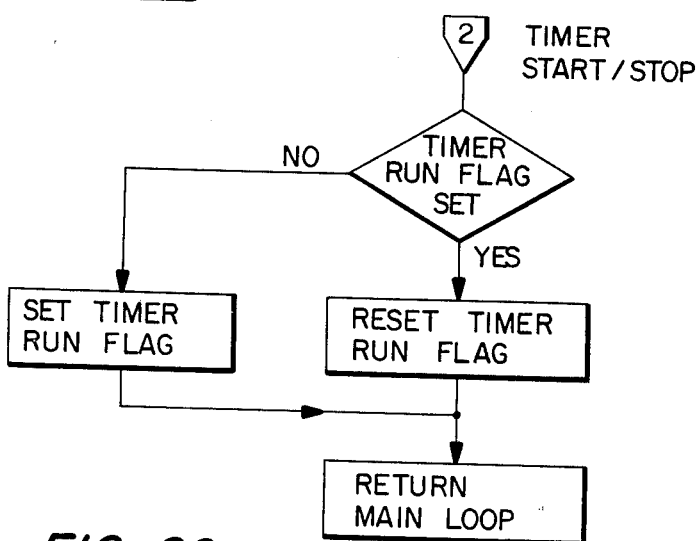
Figure 21:
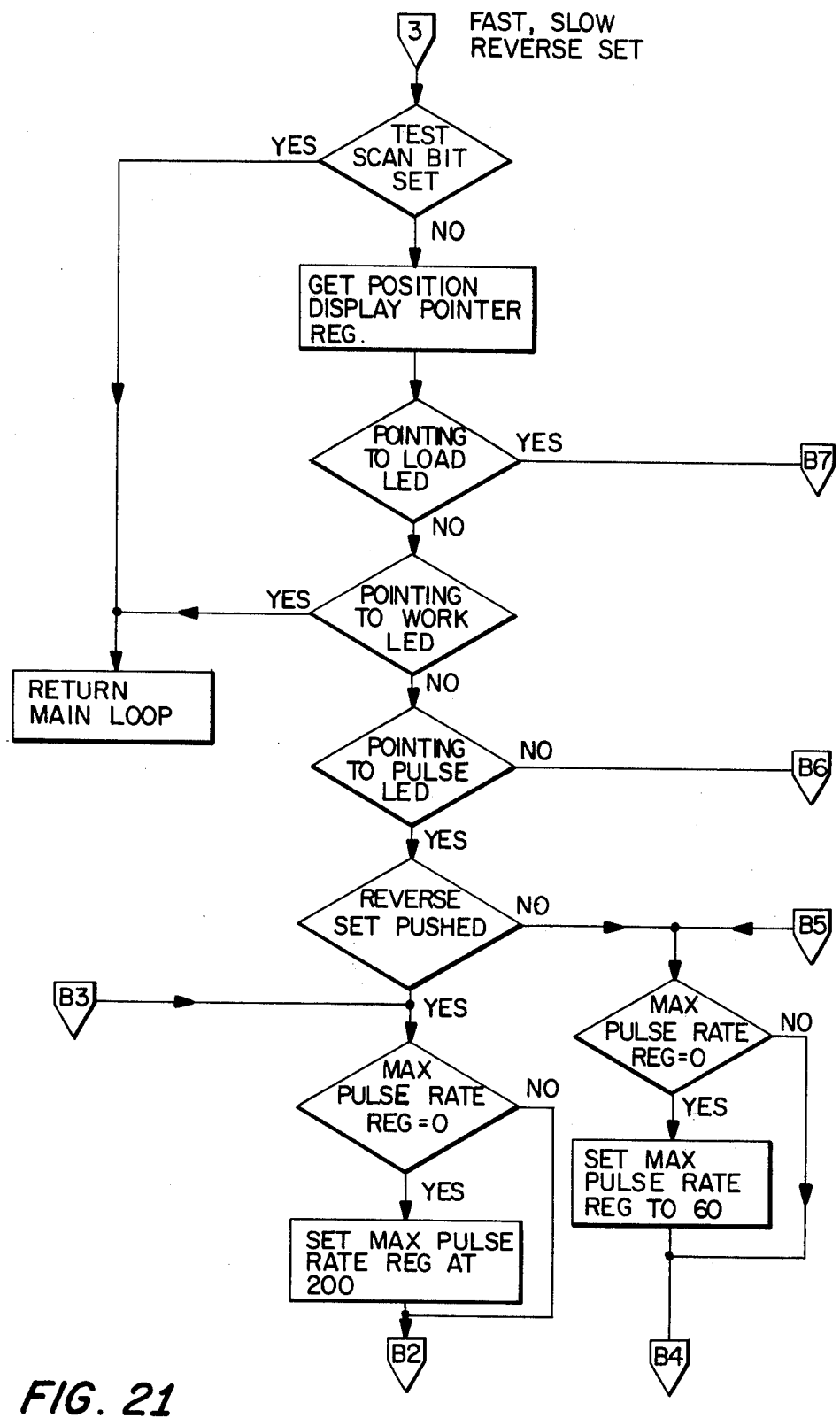
Figures 22, 23:
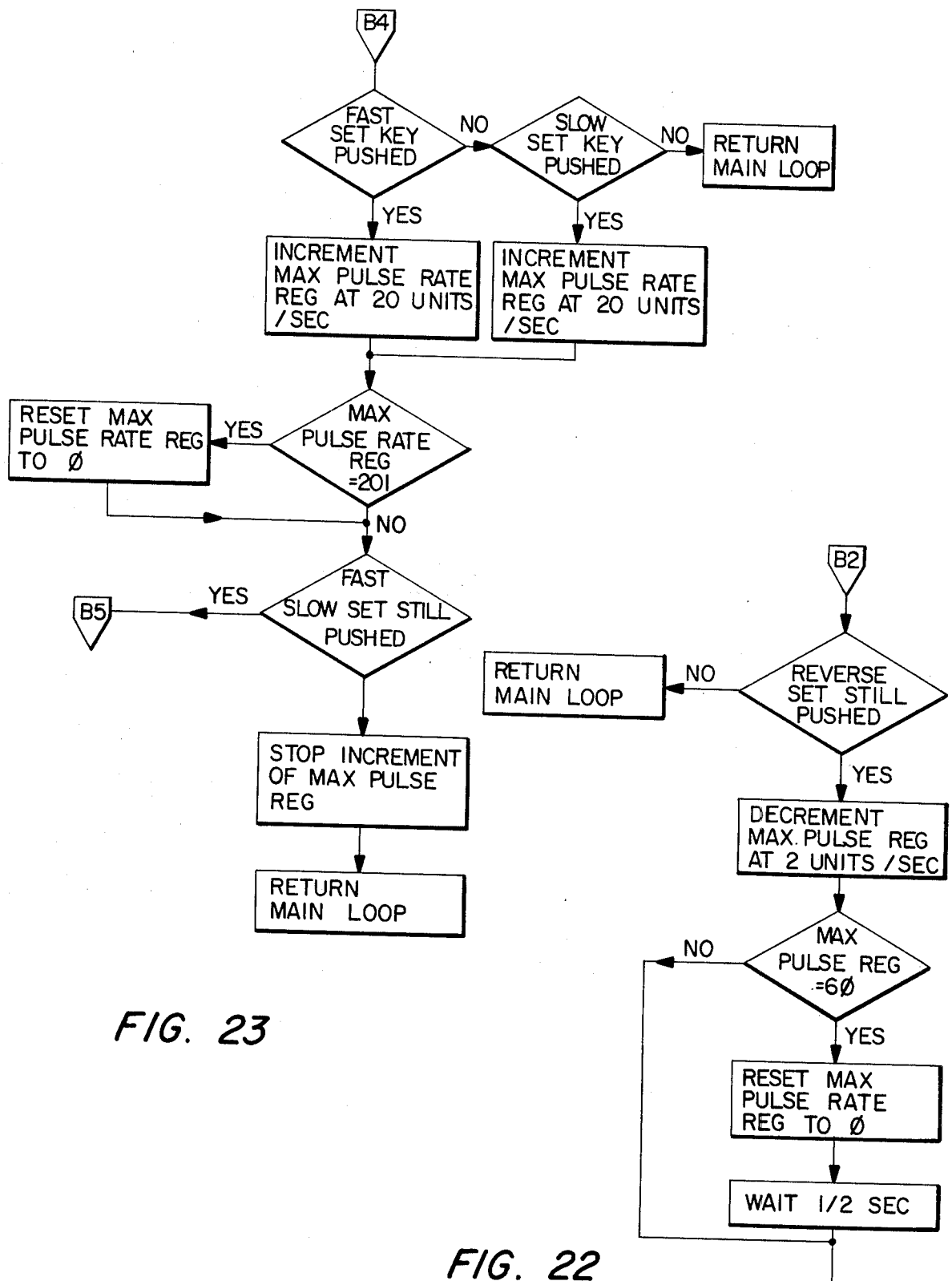
Figure 24:
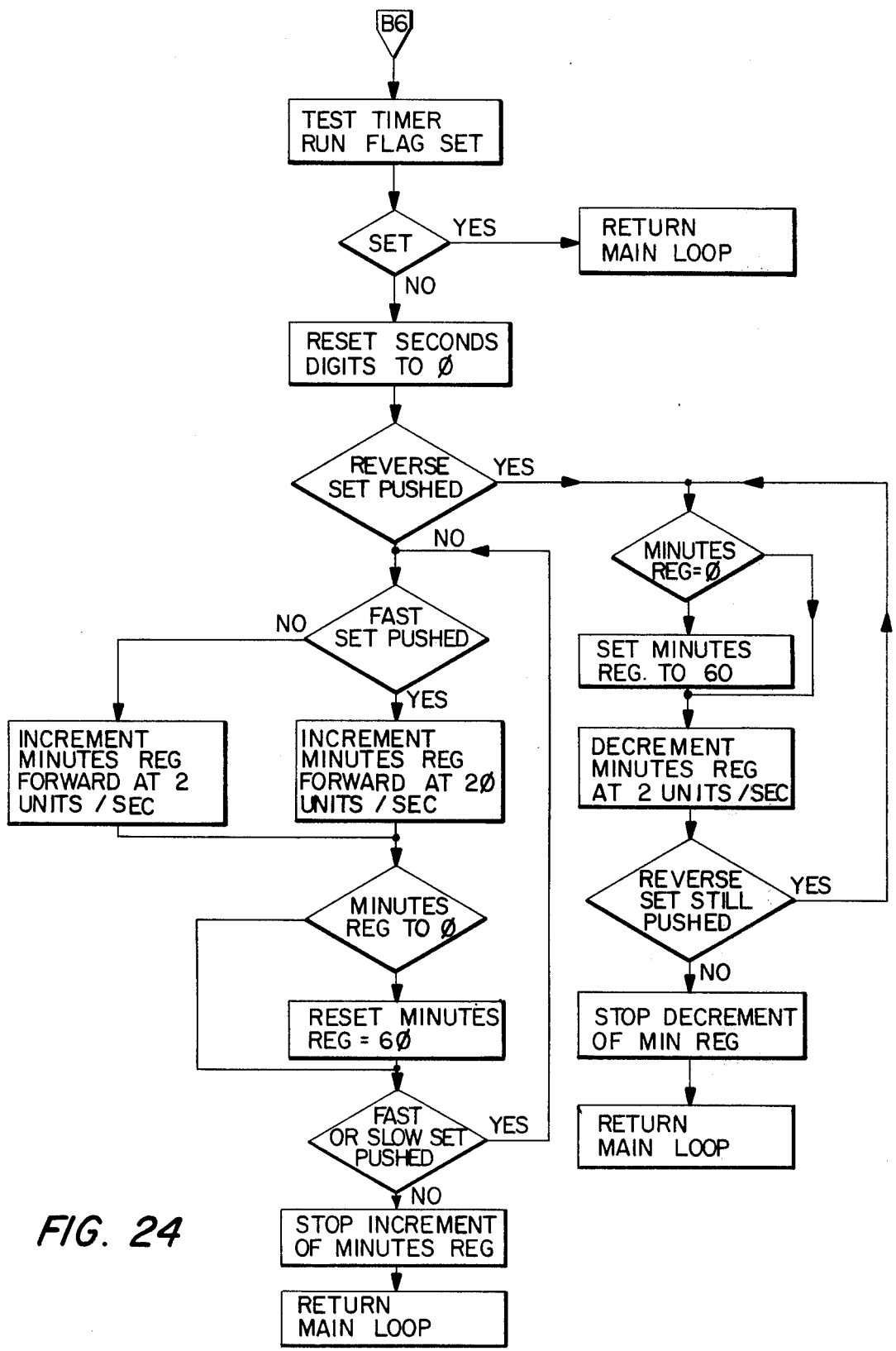
Figure 25:
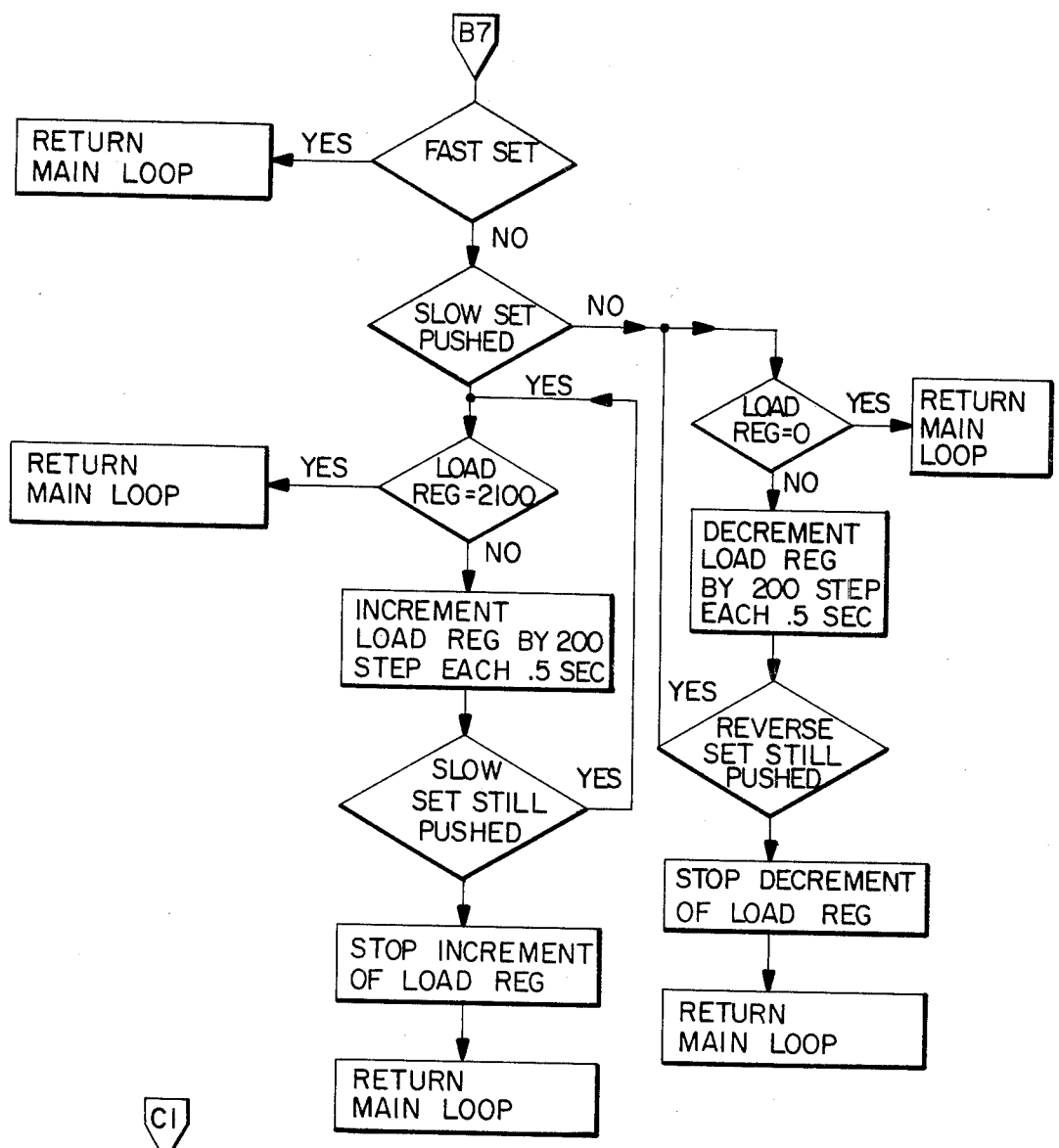
Figure 27:
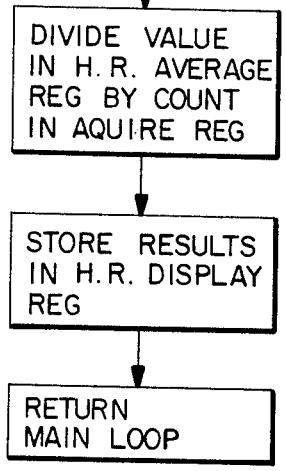
Figure 26:
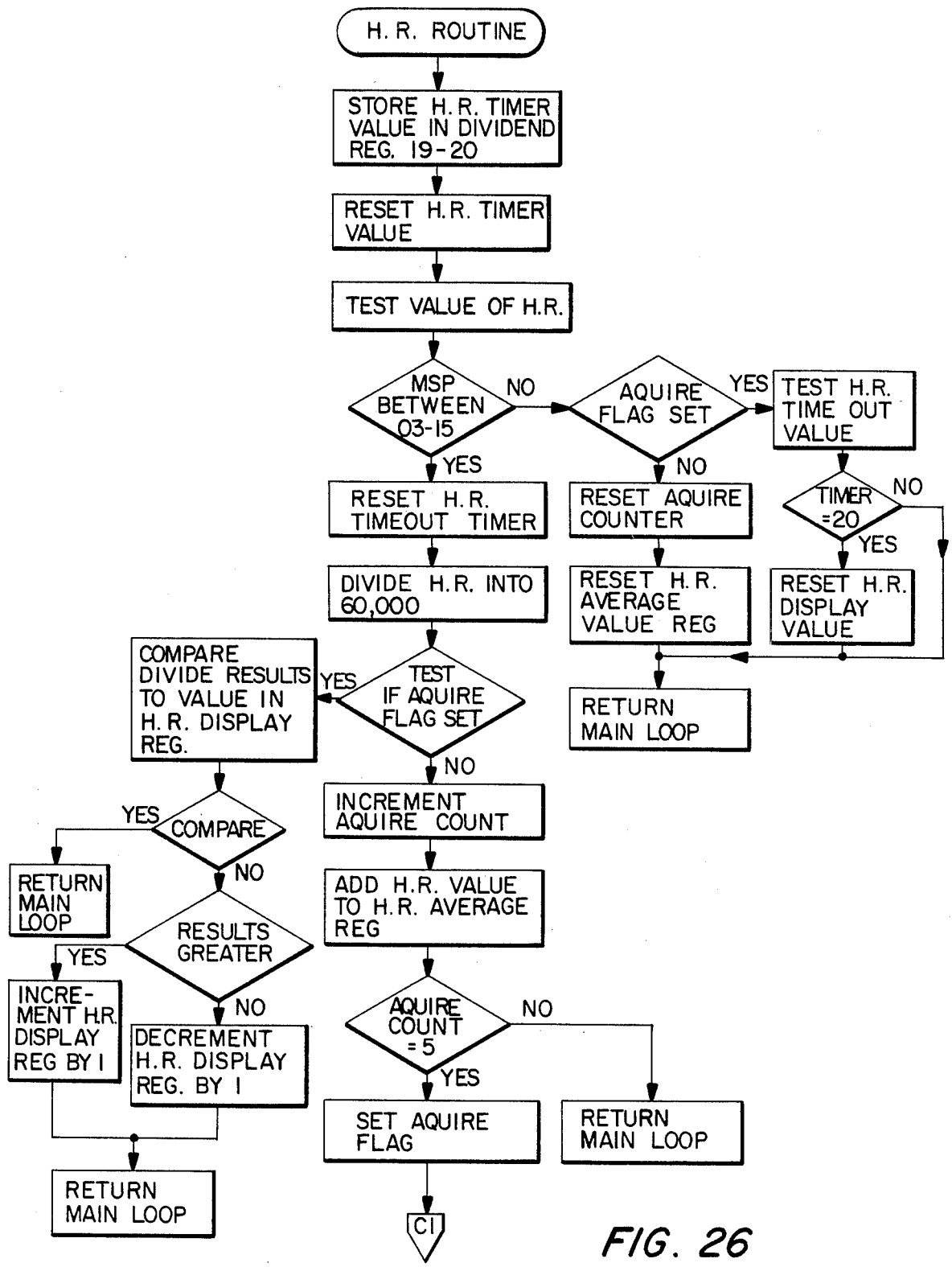

Referring in detail to FIGS. 12A through 12F, and with initial reference to FIG. 12A, additional details of the heart rate sensor circuit HRS which includes the pulse sensor 20 and the heart rate amplifier HRA will now be described and related to the remaining details of the balance of the circuit of the exerciser 10.

The light emitting diode DS1, which is the infrared source for the pulse rate sensor 20 is connected at its anode through the connector P1J1 to one end of a bias resistor R1, the latter being connected at a further end to a regulated +5 V bias voltage. The cathode of the infrared emitting diode DS1 is connected to ground through the same connector P1J1.

The phototransistor Q1 is connected at its collector through the connector P1J1 directly to the +5 V bias voltage terminal and through its emitter to the input terminal pin 10 of the chip U1 comprising the positive input terminal of the first amplifier stage U1A in the heart rate amplifier HRA. Terminal pin 10 is connected to ground through a biasing receiver R2. The terminal pins 8 and 9 of the chip U1 are connected one directly to the other thereby connecting the amplifier U1A in a voltage follower configuration with unit gain. The terminal pin 8 of the chip U1 is connected through a biasing resistor R3 to ground and through a series connected capacitor C3 and resistor R5 to the terminal pin 2 of the chip U1, the latter comprising negative the input terminal of the second stage U1B of the heart rate amplifier HRA.

Terminal pin 4 of the chip U1 is connected through a resistor R4 to the +5 V regulated source and through a pair of parallel capacitors C1 and C2 to ground. Terminal pin 11 is directly grounded. In the chip U1 at terminal pin 1, comprising the output terminal of the second amplifier stage U1B of the heart rate amplifier HRA is connected to the terminal pin 2 through a feedback loop constituting a parallel capacitor C5 resistor R6 combination.

The positive input terminal of the second stage U1B of the heart rate amplifier HRA is the terminal pin 3 of the chip U1 and is connected through a capacitor C4 to ground as well as through a resistor R7 to ground and thence directly to the terminal pin 5 of the chip U1 constituting the positive input terminal of the third stage U1C of the heart rate amplifier HRA. The terminal pins 3 and 5 are connected through a resistor R8 to the regulated +5 V voltage source.

The other input to the third stage U1C constitutes the terminal pin 6 of the chip U1 which is coupled through a resistor R9 to the terminal pin 1 of the chip U1 (output of the second amplifier stage U1B) and further is wired through a parallel resistor R10 capacitor C6 combination to the terminal pin 7 of the chip U1 (output of the third stage U1C).

The terminal pin 7 of the chip U1 is connected to ground through a bias resistor R11 and through a series connected capacitance C7 and resistance R12 to the terminal pin 12 of the chip U1 which constitutes the positive input terminal of the fourth amplifier stage U1D of the heart rate amplifier HRA. The junction between the capacitor C7 and the resistance R12 is connected to the emitter of a voltage reference control transistor Q2 which is connected with its base to collector path hardwired to ground and also connected to ground from its emitter through a bias resistor R13. The terminal pin 13 of the chip U1, constituting the negative input terminal of the fourth stage U1D is connected to ground through a biasing resistance R14 and connected to the terminal pin 14 of the chip U1, constituting the output of the fourth stage U1D, through a parallel resistance R15, capacitor C8 combination.

The terminal pin 14 of the chip U1 is connected directly to the terminal pin 2 of the chip U2 which constitutes the negative input terminal of the third comparator stage U2C, one of the four comparator amplifiers mounted on the chip U2. The terminal pin 3 of the chip U2 constitutes the positive voltage input terminal of the comparator U2C and is connected through a resistance R17 through a source of reference voltage constituting a forward biased diode CR1 which is driven through a resistance R18 by the +5 V reference voltage source. The terminal pin 3 is connected through a feedback resistance R16 to the terminal pin 1 of the chip U2 (the output terminal of the third comparator stage U2C) which through a series resistance R19 constitutes the output of the heart rate sensing circuit HRS which is applied as will be hereinafter more fully described with reference to FIG. 12B, to the terminal pin 10 of the chip U4, that chip constituting a CA3081 general purpose high current N-P-N transistor array of RCA.

Referring in detail to FIG. 12B, a portion of the microprocessor MC (also a portion of integrated circuit chip U6) constituting the input output PORT 0 is interconnected with the chip U4 as follows:

The external interrupt terminal pin 38 of the chip U6 is connected through a resistor R20 to the pin 6 of the chip U4 and directly to the pin 9 of the chip U4. The terminal pin 3 of the chip U6 constituting the PORT 0 data line 0 identified on the drawing as P0-0 is connected directly to the terminal pin 16 of the chip U4. The data line P0-1 of the PORT 0 of the chip U6 at the terminal pin 4 thereof is connected directly to terminal pin 3 of the chip U4. The data line P0-2 of the PORT 0 of the chip U6 at terminal 5 thereof is connected directly to terminal pin 14 of the chip U4 and the data line P0-3 of the PORT 0 of the chip U6 at the terminal pin 6 thereof is connected directly to the terminal pin 11 of the chip U4. Terminal pins 5 and 15 of the chip U4 are connected directly to ground the pin 15 providing a common emitter connection for all of the transistors in the chip U4. The remaining data lines P0-4, P0-5, P0-6 and P0-7 of the PORT 0 of the chip U6, respectively, occur at terminal pins 19, 18, 17, and 16 of the chip U6 and are connected, respectively, to terminal pins 7, 1, 2 and 6 of the chip U5 which constitute the A, B, C and D connections of the latter. The chip U5 has a terminal pin 8 directly connected to ground, a terminal pin 16 directly connected to the regulated source of +5 V voltage and terminals pins 3 and 5 which are commonly connected through a biasing resistor R33 to the same ±5 V regulated voltage supply.

The chip U5 is a commercially available SN 7446A BCD to 7 Segment Decoders/Drivers of Texas Instruments.

Terminal pins 1, 2, 13 and 12 of the chip U4 are connected through resistors R22, R21, R24 and R23, respectively, to terminal pins 2, 6, 13 and 9 of the chip U3, the latter comprising an MPQ 3906 P-N-P Transistor Chip. The terminal pins 3, 5, 12 and 10 of the chip U3 are connected in common to the unregulated +V supply to provide a common emitter connection for the transistors included in the chip U3.

The transistor collectors correspond to terminal pins 1, 7, 14 and 8 of the chip U3 and the terminal pins 14 and 8 are respectively connected to the common anode terminal pins 13 and 14 of a first display module DS2 corresponding to the most significant digits of the display DS while the terminal pins 1 and 7 of the chip U3 are respectively connected to the common anode terminal pins 13 and 14 of a second display module DS3 of the digital display DS representing the least significant digits thereof. Both display modules DS2 and DS3 constitute display module chips FND 6710 dual digit numeric LED displays of Fairchild.

Each of these display chips DS2 and DS3 include a series of seven segment electrodes for each digit displayable thereby which segment electrodes A1, B1, C1, D1, E1, F1 and G1 of the left most digit correspond, respectively, to terminal pins 16,15,3,2,1,18 and 17 while the second set of display segments A2, B2, C2, D2, E2, F2 and G2 of the right most digits correspond, respectively, to terminal pins 11, 10, 8, 6, 5, 12 and 7. A decimal point segment DP corresponds to terminal pin 9 of the second display module DS3. This decimal point segment and terminal pin 9 are connected through a resistor R25 directly to the terminal pin 4 of the chip U4. Thus, the decimal point segment of the second display module DS3 is responsive to conditions at the external interupt terminal pin 38 of the microprocessor MC chip U6.

As between the first and second display modules DS2 and DS3, the terminal pins 16 and 11 are commonly connected, the terminal pins 15 and 10 are commonly connected, the terminal pins 3 and 8 are commonly connected, the terminal pins 2 and 6 are commonly connected, the terminal pins 1 and 5 are commonly connected, the terminal pins 18 and 12 are commonly connected, and the terminal pins 17 and 7 are commonly connected.

Into the above common connections, via the terminal pins 16 and 11 through a resistor R27 is connected the terminal pin 13 of the encoding chip U5 corresponding to segment output a thereof; the common connection of the terminal pins 15 and 10 of the display modules DS2 and DS3 is connected through a resistor R26 to the terminal pin 12 of the code chip U5 which corresponds to the segment drive b of that chip; the common connection between terminal pins 3 and 8 of the said display module DS2, DS3 is connected through a resistors R29 to the terminal pin 11 of the code chip U5 corresponding to the segment signal c thereof; the common connection between the terminal pins 2 and 6 of the said display modules DS2, DS3 is connected through a resistor R28 to the terminal pin 10 of the code chip U5 corresponding to to the segment signal d thereof; the common connection between the terminal pins 1 and 5 of the said display modules DS2, DS3 is connected through a resistor R31 to the terminal pin 9 of the code chip U5 corresponding to the segment signals e thereof; the common connection between the terminal pins 18 and 12 of the said display modules DS2, DS3 is connected through a resistor R30 to the terminal pin 15 of the code chip U5 corresponding to the segment signals f thereof; and the common connection between the terminal pins 17 and 7 of the said display modules DS2, and DS3 is connected through a resistor R32 to the terminal pin 14 of the code chip U5 corresponding to the segment signal g thereof. This completes the interconnection of the digital display DS and the various display drivers comprised of the chips U3, U4 and U5 with the PORT 0 terminals of the chip U6 comprising the microcomputer MC and the output of the heart rate sensing circuit HRS. Therefore, all of the information which is to be shown on the digital display DS is entered thereto through the PORT 0 input/output terminals of the microcomputer MC on the chip U6.

Referring now to FIG. 12C, the balance of the visual display VD of FIG. 2 which includes the light emitting diodes indicating the load L, pulse indication P/PA, time T, and work W, also identified as diode DS4, DS5, DS6 and DS7, respectively, and the speed indication SP comprised of green and red light emitting diodes DS8 will now be described in more detail with respect to its cooperation with the PORT 1 of the chip U6 constituting the microcomputer MC.

Terminal pin 20 of the chip U6 is connected to ground while terminal pin 40 is connected to the regulated +5 V supply to provide the computer MC with a regulated logic voltage level.

Terminal pins 37, 36, 35, 34, 22, 23, 24 and 25 correspond, respectively, to input/ouput leads P1-0, P1-1, P1-2, P1-3, P1-4, P1-5, P1-6 and P1-7.

The timing signal reference for the computer MC comprises a 3.579545 MHZ crystal Y1 connected across the terminal pins 1 and 2 of the chip U6.

The chip U7, which comprises a CA 3081 General Purpose N-P-N transistor array, as previously described with respect to the chip U4, has its terminal pin 15 as the common emitter connection which is directly coupled to ground together with its terminal pin 5. Terminal pins 16, 3, 13, 11, 6, and 10, correspond, respectively, by direct connection to terminal pins 37, 36, 35, 34, 22, and 23 of the PORT 1 of the computer chip U6.

Terminal pin 8 of the chip U7 is connected through a resistor R40 to the terminal pin 4 thereof and both are then commonly connected to the anode of the green speed indicating diode in the speed indicator SP. The cathode of the two diodes DS8 are commonly connected to ground. The anode of the red light emitting diode DS8 in the speed indicator SP is connected directly to the terminal pin 7 of the chip U7. Terminal pins 1, 2, 14 and 12 are connected, respectively, to the cathodes of the light emitting diodes DS4, DS5, DS6 and DS7 corresponding to the load L, pulse P/PA, time T, and Work W indicator lamps. The anodes of these respective diodes DS4, DS5, DS6 and DS7 are connected to +V unregulated supplies through respective resistors R35, R34, R37 and R36.

The anodes of the green and red diodes DS8 of the speed indicator SP are connected through resistors R38 and R39, respectively, to the +V unregulated supply.

The terminal pin 9 of the chip U7 constitutes an output signal terminal which drives terminal pins 6 of the chip U2 which constitutes the negative input of the fourth comparator amplifier U2D. The terminal pin 6 of the chip U2 is also connected through a capacitance C9 to ground. The terminal pin 5 of the chip U2 constituting the positive input terminal of the fourth comparator amplifier U2D is connected through a resistor R42 to ground and through a resistor R41 to the +V unregulated supply. It is also connected through a resistor R43 to the terminal pin 7 of the chip U2 which constitutes the output terminal of the fourth comparator amplifier U2D. This terminal pin 7 is also connected through a resistor R44 to both the terminal pin 6 of the chip U2 and the terminal pin 9 of the chip U7.

Ultimately, by direct connection, the terminal pin 7 of the chip U2 constituting the output terminal of the fourth comparator amplifier U2D is directly connected to the audio alert means or sonic alarm SA which is sounded when the pulse of the user of the exerciser 10 exceeds predetermined safe limits.

Terminal pin 24 of the microcomputer chip U6 corresponding to the input/output line P1-6 of the PORT 1 thereof is connected as a test lead to the connection devices J2, J4 at the remote display select switch S6. The interconnect device J2, J4 is also interrelated with with the connection devices J2, J3 of the power circuit of FIG. 12F, to be hereinafter more fully described, for the purpose of initiating a test of the various functions of the device in the event of breakdown or for manufacturing and quality control purposes.

The terminal pin 25 of the chip U6 corresponding to the PORT 1 input output lead P1-7 is connected directly to terminal pin 4 of a chip U8 in FIG. 12D, to which reference will now be had for the purpose of receiving an alternator load signal $\overline{\text{AT LOAD}}$ from the output of the low speed comparator U2B of the chip U2 which will be described in more detail with respect to FIGS. 12D and 12E.

Referring now to FIG. 12D, the input/output PORT 4 and input output PORT 5 of the computer chip U6 of the microcomputer MC and the cooperation of these PORTs 4 and 5 with the display select, start, fast set, slow set, and back set switches S1-S5, respectively, together with the multiplicity of load range connections determined by input leads CL (11 in number), previously described in reference to FIG. 5, inputing to the digital-to-analog converter DAC in the electronic load circuit EL, will now be described.

The digital-to-analog converter DAC consists of circuit chip U8 and U9, each comprising a CA3081 general purpose N-P-N transistor array previously defined with respect to the circuit chip U4 and U7, and which are interconnected with the computer chip U6 as follows:

The terminal pins 15 of the chips 8 and 9 comprise the common emitter connections for each chip and are connected to ground as are the terminal pins 5 of each of these chips. Terminal pin 4 of the chip U8 has already been defined as connected to the terminal pin 25 (the input/output line P1-7) of the PORT 1 on the computer chip U6 in FIG. 12C and terminal pin 6 of the chip U8 as being connected to R59 and therethrough to the terminal pin 8 of the chip U2 constituting the output terminal of the second comparator amplifier U2B in FIG. 12E.

Terminal pins 11, 13 and 3 of the chip U8 are respectively connected to terminal pins 13, 14 and 15 of the computer chip U6 which correspond, respectively, to the input output leads P4-5, P4-6 and P4-7 of the PORT 4. Terminal pin 16 of the chip U8 is connected to the terminal pin 26 of the computer chip U6 which corresponds to the input/output line P5-7 of the input output PORT 5. Terminal pin 12 of the chip U8 is directly connected to a terminal pin 12 of the chip U2, constituting the positive input of the first comparator amplifier U2A as well as through a resistance R55 to the cathode of a voltage regulating device CR2 and one side of a capacitance C10, the opposite side of the capacitance C10 and the anode of the voltage regulating device CR2 being connected to ground. The voltage regulating device CR2 also is shunted by resistors R57 and R58 extending from the cathode to the anode thereof with the common point between the two resistors being connected to a gate or bias terminal on the voltage regulating device CR2. The cathode of the voltage regulating device CR2 is also connected through a resistor R56 to the source +V of unregulated voltage. Thus, the voltage generated across the capacitor C10 is the reference voltage Vref for the first and second reference amplifiers U2A and U2B and is applied to the terminal pin 12 of the chip U2 through resistor R55 and thence to the terminal pin 9 of the chip U2 through a resistor R65 in series with the resistor R55. The terminal pin 9 of the chip U2 (the negative input terminal of the second comparator amplifier U2B) is connected to ground through a biasing resistor R61, as shown in FIG. 12E.

The reference voltage from the terminal pin 12 of the chip U2 (FIG. 12E and FIG. 12D) is applied through a resistor R45 to the terminal pin 14 of the chip U8, a resistor R46 to the terminal pin 2 of the chip U8, and a resistor R47 to the terminal pin 1 of the chip U8. The reference voltage is also applied to terminal pins 1, 2, 14, 12, 4, 9 and 7 of the chip U9 through resistors R48, R49, R50, R51, R52, R53, and R54, respectively.

The terminal pin 16, 3, 13, 11, 6, 10 and 8 are directly connected, respectively, to the terminal pins 33, 32, 31, 30, 29, 28, and 27 of the computer chip U6 corresponding to input/output leads P5-0, P5-1, P5-2, P5-3, P5-4, P5-5 and P5-6 of the PORT 5.

The display select switch S1 is connected between ground and the terminal pin 8 of the computer chip U6 corresponding to the input/output lead P4-0 of the PORT 4. The start switch S2 for the exercise time function is connected from ground to the terminal pin 9 of the PORT 4 corresponding to the input/output lead P4-1 thereof; the fast set switch S3 is connected from ground to the terminal pin 10 corresponding to the input/output P4-2 of the PORT 4; slow set switch S4 is connected from ground to the terminal pin 11 corresponding to the input/output lead P4-3 of the PORT 4; and the back set or reverse set switch S5 is connected from ground to the terminal pin 12 corresponding to the input/output lead P4-4 of the PORT 4, all on the computer chip U6. The connectors J2 and J4 and the remote display select switch S6 are also illustrated in FIG. 12D with the positive voltage lead, or nonground lead, extending therefrom to the terminal pin 8 of the PORT 4 of the computer chip U5, namely, the identical terminal pin that the display select switch S1 in the control console 22 is connected with.

Referring now to FIG. 12E the alternator M1 is shown as having a field terminal F connected to the emitter of a transistor Q4 which is in a common collector configuration with the transistor Q3 and both collectors are directly wired to the source of unregulated voltage +V. The emitter of the transistor Q3 is connected to the base of transistor Q4 to provide a field current source configuration for controlling the load provided to the user of the exerciser 10 at the shaft M1A of the alternator M1. The alternator includes positive and negative output terminals which are joined together by load resistor R68 with the negative terminal constituting the ground terminal and the output of the alternator being through selfcontained rectifiers, as is typical of automotive style alternators. The positive alternator terminal is connected through the interconnection device J2 through a resistor R63 and thence through resistors R64 and R62, respectively, to terminal pins 13 and 10 of the chip U2, the said terminal pins 13 and 10 corresponding, respectively, to the negative input terminal of the first comparator amplifier U2A and the positive input terminal of the second comparator amplifier U2B. The terminal pin 13 of the chip U2 is connected to the terminal pin 14 thereof through a resistor R66 while the terminal pin 4 is connected to the +V unregulated voltage supply and the terminal pin 11 is grounded. This completes the circuit connections for the first comparator amplifier U2A having its output terminal corresponding to the terminal pin 14 of the chip U2 and which is connected through the resistor R67 to the base of the first transistor Q3 in the current source configuration Q3, Q4 driving the field terminal F of the alternator M1.

The terminal pins 8 and 10 of the chip U2 are connected together through a resistor R60 and the junction between the resistors R62 and R63 is connected to ground through a capacitor C11 to complete the circuit interconnections for the second comparator amplifier U2B in the chip U2 with the balance of the electronic load control circuit EL of FIG. 12E.

The power supply providing the unregulated voltage +V and the regulated logic level +5V to the exerciser 10 of the present invention and the microcomputer MC therein is illustrated with reference to FIG. 12F which includes the ON/OFF switch S7 connected between the diagonal terminals of a full wave bridge rectifier CR3, CR4, CR5, CR6 in series with the secondary of a transformer T1. The other diagonal connection of the bridge rectifier is connected at one side to ground and at its other side across first and second parallel capacitors C12 and C13 and a series resistor 69 capacitor C14 branch, all to ground, with the common terminal between the resistor R69 and capacitor C14 driving the input terminal of a regulating device U10 corresponding to a commercially available voltage regulator module 7805 such as UA 7805 C of Texas Instruments. One terminal of the chip U10 is grounded and the output terminal is connected to one side of a smoothing capacitor C15 (the latter having its other end grounded) which constitutes the +5V regulated output. The output of the diagonal terminal connected through the resistor R69 to the input terminal of the device U10 constitutes the +V unregulated output voltage. The primary of the transformer T1 is shown as connected to a 120 volt A.C. source of + or −10% accuracy and includes a ground lead GRD. This completes the detailed description of the electronic circuitry of the exerciser 10 of the present invention.

TYPICAL EXERCISE SESSION

The functional operation of the ergometric exerciser of the present invention will now be explained by describing a typical exercise session.

Programming the Exerciser

The user connects the pulse sensor 20 and the power unit 18 to the exerciser 10 as previously described with reference to FIG. 1, sits on the exerciser 10 and clips the pulse sensor 20 over either ear lobe. The POWER switch S7 is then turned ON. The DISPLAY SELECT switch S1 is used to turn ON the LOAD LED L. Then the SET buttons S3, S4, S5 are utilized to select a load such as 500 kpm/min.

Next the user actuates DISPLAY SELECT switch S1 to select the PULSE/PULSE ALERT function and illuminate LED P/PA. The pulse sensor 20 is positioned over the fleshy part of the ear lobe. After about 15 seconds a pulse rate reading will be displayed on digital display DS and the decimal point in the last digit of the numerical display thereon will flash in synchronism with the users pulse. Each time the decimal dot flashes the numerical display will be updated and may change by ±1 digit. The user's pulse rate is calculated on a beat-by-beat basis by the microcomputer MC but the display DS is allowed to change by only 1 digit for each update in order to "average" the instantaneous pulse rate. It is normal for the user's pulse rate to vary from beat-to-beat and this would be confusing if the digital readout was not averaged.

If desired the PULSE ALERT function can now be activated by pushing any of the SET buttons S3, S4, S5. By way of example, the SLOW SET button S4 is chosen. As soon as switch S4 is pushed, a half size "U" symbol appears in the left most digit and the DIGITAL DISPLAY DS will increment, 0. 60, 61, 62, ... 199, 200, 0 one digit at a time. Assume for the purposes of explanation that a pulse limit of 125 is chosen. (Information has been published by other sources to allow a user to determine a desirable pulse limit related to age and physical condition, etc.) If the user overruns the desired setting the FAST SET and REVERSE SET buttons S3, S5 can be used in combination with the SLOW SET button S4 to return to the value desired.

Next the exercise time period can be set by sequencing the LEDs using the DISPLAY SELECT button S1 until the TIME LED T is ON. Again using the three SET buttons S3, S4, S5 the timer may be set to the desired value, such as 2:00 minutes. The timer can only be set when it is stopped. If it is counting up or down, the SET buttons S3, S4, S5 have no effect. In addition, the use of the timer function is optional and the other functions of the exerciser 10 are independent of the timer and can still be used.

The exerciser 10 is now programmed after completion of the above steps and the exercise session can begin. At this time the SPEED LED SP will be alternately flashing red and green. This is the low pedal speed indication and warns the user that he is not pedaling fast enough to generate sufficient electrical output from the alternator M1. When the pedal speed of pedal assembly 16 is above the minimum, the SPEED LED SP will stop flashing red/green and will give a steady green indication only.

Initially the work displayed on DS reads zero since no work has been done yet. When actual exercising starts, the microcomputer MC will begin to compute and accumulate the work done in kpm×10. The computer MC computes and updates the work display once each second.

Exercising Routine

When the user is ready to start the actual exercise period, the TIMER START/STOP button is pushed (if the user has opted to use the timer function) and pedaling may begin. The rate at which the user pedals can vary as long as it is faster than the minimum rate as indicated by a steady green indication on the SPEED LED SP. It is not at all difficult to pedal at the required speed. If the WORK function is still selected as indicated by LED W, the WORK displayed on digital display DS will begin to increase. The DISPLAY SELECT button S1 may be used any time to select a different display function such as LOAD, PULSE/PULSE ALERT or TIME. During actual exercising, the user may find it more convenient to use the remote DISPLAY SELECT swith S6 mounted on the handlebars to sequence the LEDs L, P/PA, T, W which signify the units and data mode displayed by digital display DS. Either switch S1 or S6 can be used interchangeably to sequence the display.

If the user wants to increase (or decrease) the amount of work loading while exercising, the user may simply use the DISPLAY SELECT (S1, S6) and the SET pushbuttons (S3, S4, S5) as desired. The microcomputer MC automatically corrects its computation for the work load range selected. If the user stops pedaling for any reason, it may be desirable to stop the timer by pushing the TIMER START/STOP button S2. The TIMER START/STOP button S2 is active at all times, not just when the TIME readout is selected. The timer function as stated hereinbefore is independent of all other exerciser functions.

If during the exercise session, the user's pulse rate equals the preset pulse limit value, the sonic alarm SA will sound a "beeping" tone for as long as the limit value is equaled or exceeded. If desired, the pulse limit value can be changed higher or lower during the exercise session. If, during use, the pulse sensor 20 does not receive a valid pulse signal for any reason, then after a 15 second delay, the DIGITAL DISPLAY DS is reset to zero to warn the user of this condition. The loss of the pulse signal would occur, for example, if the pulse sensor 20 inadvertently slipped off the ear lobe or if its position changed so that a proper signal was not obtained.

The exercise session is over when the TIME LED T flashes or the TIME display on digital display DS counts down to zero. At this point the user can stop exercising and use the pulse and time readouts to determine the length of time it takes for the pulse rate to return to the resting rate. Or one may continue to exercise, simply letting the timer count up or alternately setting in additional time. The accumulated work total is only reset when the exerciser POWER switch S7 is turned OFF. Therefore, if several users will be exercising during one session, it may be convenient to momentarily switch the power off between users in order to reset the accumulated work to zero.

If the exerciser is not pedaled for a period of five minutes, the microcomputer MC turns off the field current of the alternator to reduce internal heating and resets the LOAD value to zero to indicate this time-out condition. If this condition has occurred, it will be necessary to reprogram the desired work loading before using the exerciser again.

In accordance with the above, the term "lamps are positioned in a line" describes the relative (physical) position of the lamps on the control panel 22. The term "constant work" means essentially maintaining a selected amount of work performed or capable of being performed within a specific period.

It should be understood that, although the preferred embodiment of the system described herein utilizes a microcomputer as a central control means, the entire system may be hardwired with standard electronic components, as would occur to one of ordinary skill in the art, to perform all of the functions described hereinbefore without departing from the spirit and scope of the present invention.

The following data sheets on the commercially available integrated circuit chips utilized with the present invention as described hereinbefore with reference to FIGS. 12A to 12F are incorporated by reference into the disclosure of this application.

Data Sheet IC 3870 (F 3870, Fairchild, pgs. 1 to 19)

Data Sheet ICSN7446 (Texas Instruments, pgs. 7-22 to 7-34)

Data Sheet IC CA 3081 (RCA File No. 480, pgs. 399-401)

Data Sheet IC 7805 (Texas Instruments Series uA 7800, pgs 149 to 155)

Data Sheet IC LM 2902 (National Semiconductor, Quad Op Amps, pgs 2-242 to 2-249)

Data Sheet IC MAN 6710 (Fairchild FND 6710, FND 6730, "Dual Digit Numeric Displays", November, 1977)

Data Sheet MPQ 3906 (Quad Dual-in-Line PNP Silicon Annular Amplifier/Switch Transistor, Motorola, pgs 844,845)

Although any suitable software may be used, applicant's computer software printout of the program represented by the flow chart of FIGS. 13 to 27, is incorporated by reference into the disclosure of this application.

It is noted further, that a copy of each of the above referenced documents are on file with the Patent and Trademark Office in connection with the disclosure of this application for review of the public upon request.

What is claimed is:

1. An ergometric exercise device having a pedal assembly operated by a user, a work generator coupled to the pedal assembly for providing a controlled amount of resistance to operation of the pedal assembly, and a control panel for inputting and outputting data from said device in a plurality of selected data modes, the improvement comprising:

numerical display means for indicating the magnitude of data for each of said selected data modes;

signal means for indicating which of said data modes has been selected and the units of the data displayed on said numerical display means, said signal means including a signal lamp associated with each of said data modes and circuit means for imparting a different energization state to a selected signal lamp associated with a selected data mode than to the signal lamps associated with the other data modes, said different energization state of said selected signal lamp signifying to a user that said numerical display is displaying units corresponding to said selected data mode; and selector switch means constraining said circuit means to sequentially transfer said different energization state from one signal lamp to another in response to each actuation of said selector switch means, said transfer occurring in a predetermined sequence; and data input means for at least two of said data modes for enabling the user to preset input data into said circuit means.

2. The invention according to claim 1, wherein said signal lamps are positioned in a line and said predetermined sequence is from one end of said line to the other, seriatim.

3. The invention according to claim 1 further including data input means for each of said data modes for presetting input data into said circuit means comprising:

first switch means for incrementing said numerical display until a desired value is displayed thereon.

4. The invention according to claim 3, further including second switch means for decrementing said numerical display until a desired value is displayed thereon.

5. The invention according to claim 3, wherein said first switch means includes a fast set switch and a slow set switch, said fast set switch incrementing said numerical display at a faster rate than said slow set switch.

6. The invention according to claim 1, further including means for generating an indicating flag on said numerical display means in response to said data input means for distinguishing input data from output data.

7. The invention according to claim 1 further including a power switch means and means within said circuit means for generating a test pattern on said numerical display and said signal lamps for a predetermined time after said power switch means is first turned ON.

8. The invention according to claim 1, wherein one of said data modes comprises a timing mode for indicating the duration of an exercise routine, said duration being presettable by said data input means, said circuit means including means for flashing the signal lamp associated with said timing mode ON and OFF when said presettable duration has been exceeded.

9. The invention according to claim 1, wherein said work generator generates constant work above a predetermined pedal speed and means are provided on said control panel for visually signalling the user as to whether the pedal speed is above or below said predetermined speed.

10. The invention according to claim 1, wherein one of said data modes is a pulse rate monitoring mode for displaying a current pulse rate of the user on said numerical display and for determining when a predetermined pulse rate is exceeded, said predetermined pulse rate being preset on said numerical display by said data input means, and means are provided for comparing said current pulse rate with said predetermined pulse rate and generating an alarm when said current pulse rate exceeds said predetermined pulse rate.

11. The invention of claim 1, wherein said circuit means comprises a microcomputer and associated electronic interface means between said microcomputer and said control panel.

12. The invention according to claim 11, wherein said microcomputer includes means for calculating work performed by a user of said exerciser.

13. The invention according to claim 11, wherein said microcomputer includes means for computing the user's average pulse rate.

14. The invention defined in any one of claims 3, 4, 5, 6, 7, 8, 9, 10 and 11, wherein said signal lamps are positioned in a line and said predetermined sequence is from one end of said line to the other, seriatim.

15. The invention defined in any one of claims 3, 4, 5, 7, 8, 9, 10 and 11, further including means for generating an indicating flag on said numerical display means in response to said data input means for distinguishing input data from output data.

16. The invention defined in any one of claims 3, 4, 5, 8, 9, 10 and 11 further including a power switch means and means within said circuit means for generating a test pattern on said numerical display and said signal lamps for a predetermined time after said power switch means is first turned ON.

17. The invention defined in any one of claims 3, 4, 5, 9, 10 and 11 wherein one of said data modes comprises a timing mode for indicating the duration of an exercise routine, said duration being presettable by said data input means, said circuit means including means for flashing the signal lamp associated with said timing mode ON and OFF when said presettable duration has been exceeded.

18. The invention defined in any one of claims 3, 4, 5, 10 and 11, wherein said work generator generates constant work above a predetermined pedal speed and means are provided on said control panel for visually signalling the user as to whether the pedal speed is above or below said predetermined speed.

19. The invention defined in any one of claims 3, 4, 5 and 11, wherein one of said data modes is a pulse rate monitoring mode for displaying a current pulse rate of the user on said numerical display and for determining when a predetermined pulse rate is exceeded, said predetermined pulse rate being preset on said numerical display by said data input means, and means are provided for comparing said current pulse rate with said predetermined pulse rate and generating an alarm when said current pulse rate exceeds said predetermined pulse rate.

20. The invention defined in any one of claims 3, 4 and 5, wherein said circuit means comprises a microcomputer and associated electronic interface means between said microcomputer and said control panel.

21. The invention defined in any one of claims 2, 3, 4, 5, 6, 7, 8, 9 and 10, wherein said circuit means comprises a microcomputer and associated electronic interface means between said microcomputer and said control panel; and
wherein said microcomputer includes means for calculating work performed by a user of said exerciser.

22. The invention defined in any one of claims 2, 3, 4, 5, 6, 7, 8, 9 and 10, wherein said circuit means comprises a microcomputer and associated electronic interface means between said microcomputer and said control panel; and
wherein said microcomputer includes means for computing the user's average pulse rate.

23. The invention defined in any one of claims 2, 3, 4, 5, 6, 7, 8, 9 and 10, wherein said circuit means comprises a microcomputer and associated electronic interface means between said microcomputer and said control panel;
wherein said microcomputer includes means for calculating work performed by a user of said exerciser; and
wherein said microcomputer includes means for computing the user's average pulse rate.

24. The invention of claim 1, wherein said circuit means comprises a microcomputer and associated electronic interface means between said microcomputer and said control panel;
wherein said microcomputer includes means for calculating work performed by a user of said exerciser; and
wherein said microcomputer includes means for computing the user's average pulse rate.

25. The invention of claim 1, further including data input means for each of said data modes for presetting input data into said circuit means comprising:
first switch means for incrementing said numerical display until a desired value is displayed thereon, said first switch means includes a fast set switch and a slow set switch, said fast set switch incrementing said numerical display at a faster rate than said slow set switch; and
second switch means for decrementing said numerical display until a desired value is displayed thereon.

* * * * *